(12) United States Patent
Liu et al.

(10) Patent No.: US 12,090,213 B2
(45) Date of Patent: Sep. 17, 2024

(54) SMART EXOSOMES FOR ACTIVE PDAC TARGETING AND EVADING MONONUCLEAR PHAGOCYTOTIC SYSTEM

(71) Applicant: The University of Toledo, Toledo, OH (US)

(72) Inventors: Shi-He Liu, Toledo, OH (US); Francis Charles Brunicardi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 18/550,503

(22) PCT Filed: Mar. 17, 2022

(86) PCT No.: PCT/US2022/020728
§ 371 (c)(1),
(2) Date: Sep. 14, 2023

(87) PCT Pub. No.: WO2022/197911
PCT Pub. Date: Sep. 22, 2022

(65) Prior Publication Data
US 2024/0042055 A1 Feb. 8, 2024

Related U.S. Application Data

(60) Provisional application No. 63/162,589, filed on Mar. 18, 2021.

(51) Int. Cl.
*A61K 47/69* (2017.01)
*A61K 47/64* (2017.01)

(52) U.S. Cl.
CPC ...... *A61K 47/6901* (2017.08); *A61K 47/6425* (2017.08)

(58) Field of Classification Search
None
See application file for complete search history.

(56) References Cited

FOREIGN PATENT DOCUMENTS

WO 2018018077 A1 2/2018

OTHER PUBLICATIONS

Garcia, et al. (2021) "Harnessing Macrophages through Blockage of CD47: Implications for Acute Myeloid Leukemia", Cancers, 13: 6258, 13 pages long. (Year: 2021).*
Luan et al., "Engineering exosomes as refined biological nanoplatforms for drug delivery", Acta Pharmacologica Sinica, (2017), Issue No. 38, pp. 754-763.
Liu et al., "Genetically engineered exosomes enable active pancreatic cancer targeting and evading mononuclear bhagocytic system", American Association for Cancer Research, (2020), abstract.
Kamerkar et al., "Exomes Facilitate Therapeutic Targeting of Oncogenic Kras in Pancreatic Cancer", Nature, Pubmed, (2017), pp. 1-41.
Nam et al., Emerging Prospects of Exosomes for Cancer Treatment: From Conventional Therapy to Immunotherapy, Advanced Materials, Pubmed, (2020), abstract; pp. 1-37.
Hulme et al., "Distinct Regions of the Large Extracellular Domain of Tetraspanin CD9 Are Involved in the Control of Human Multinucleated Giant Cell Foundation", PLOS ONE, (2014), pp. 1-17.
Thermofisher Scientific, "Jump In™ T-REx™ HEK 293 Kit", retrieved from the internet <URL: https://web.archive.org/web//20200811105315/https://www.thermofisher.com/order/catalog/product/A15008>.
PCT International Search Report and Written Opinion, Application No. PCT/US22/20728, dated Aug. 11, 2022.

* cited by examiner

*Primary Examiner* — Robert M Kelly
(74) *Attorney, Agent, or Firm* — MacMillan, Sobanski & Todd, LLC

(57) ABSTRACT

Exosomes that express peptides in CD9 proteins, and smart exosomes that co-express two peptides incorporated into CD9 proteins to home delivery of the exosomes to a desired target and evade phagocytosis by macrophages, are described. Provided are exosomes useful for delivering drugs to desired targets. The exosomes comprise drugs, such as chemotherapeutic drugs, encapsulated in their core. The targets include pancreatic cancer cells.

14 Claims, 43 Drawing Sheets
(24 of 43 Drawing Sheet(s) Filed in Color)
Specification includes a Sequence Listing.

SMART EXOSOMES FOR ACTIVE PDAC TARGETING AND EVADING MONONUCLEAR PHAGOCYTOTIC SYSTEM

RELATED APPLICATIONS

This is the national phase entry of international application PCT/US2022/020728, filed under the authority of the Patent Cooperation Treaty on Mar. 17, 2022, published; which claims priority to U.S. Provisional Application No. 63/162,589, filed under 35 U.S.C. § 111(b) on Mar. 18, 2021. The entire disclosure of each of the aforementioned applications is hereby incorporated herein by reference for all purposes.

SEQUENCE LISTING

The instant application contains a Sequence Listing which has been submitted electronically in ASCII format and is hereby incorporated by reference in its entirety. The ASCII copy, created on Mar. 16, 2022, is named 62534-WO-PCT_SL.txt and is 2,105 bytes in size.

STATEMENT REGARDING FEDERALLY SPONSORED RESEARCH

This invention was made with no government support. The government has no rights in this invention.

BACKGROUND

Therapies for pancreatic cancer are largely hindered by the lack of an effective delivery system. Three major concerns include safety, active cellular targeting, and clearance by the mononuclear phagocytotic system (MPS). There remains a need in the art for new and improved compositions and methods for treating pancreatic cancer.

SUMMARY

Provided is a composition comprising an exosome that expresses a peptide on a surface of the exosome, wherein the peptide is incorporated into a CD9 protein.

In certain embodiments, the peptide is incorporated into an extracellular loop of the CD9 protein. In certain embodiments, the peptide is incorporated into a variable region of a large extracellular loop of the CD9 protein. In certain embodiments, the peptide is incorporated at the E174 residue of the CD9 protein. In certain embodiments, the peptide is incorporated at the V178 residue of the CD9 protein.

In certain embodiments, the peptide comprises RGD. In certain embodiments, the peptide consists of RGD. In certain embodiments, the peptide comprises a CD47 peptide. In certain embodiments, the peptide comprises a $CD47^{p110-130}$. In certain embodiments, the peptide consists of $CD47^{p110-130}$. In certain embodiments, the peptide is labeled or tagged.

In certain embodiments, the exosome further comprises a second peptide expressed on the surface of the exosome, wherein the second peptide is incorporated into a second CD9 protein. In particular embodiments, the second peptide is incorporated into an extracellular loop of the second CD9 protein. In particular embodiments, the second peptide is incorporated into a variable region of a large extracellular loop of the second CD9 protein. In particular embodiments, the second peptide is incorporated at the E174 residue of the second CD9 protein. In particular embodiments, the second peptide is incorporated at the V178 residue of the second CD9 protein. In particular embodiments, the first peptide comprises RGD, and the second peptide comprises a CD47 peptide. In particular embodiments, the first peptide comprises RGD, and the second peptide comprises $CD47^{p110-130}$.

In certain embodiments, the exosome is about 100 nm in diameter. In certain embodiments, the exosome is produced from human embryonic kidney (HEK) 293 cells.

In certain embodiments, the exosome further comprises a drug encapsulated in a core. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

In certain embodiments, the first peptide comprises RGD, the second peptide comprises $CD47^{p110-130}$, and the exosome further comprises a drug comprising a chemotherapeutic agent encapsulated therein. In certain embodiments, the first peptide comprises RGD, the second peptide comprises $CD47^{p110-130}$, and the exosome further comprises paclitaxel encapsulated therein.

Further provided is a method for delivering a drug to pancreatic cancer cells, the method comprising loading an exosome that co-expresses RGD and $CD47^{p110-130}$ in CD9 proteins with a drug to obtain a drug-loaded exosome; and administering the drug-loaded exosome to a subject having pancreatic cancer to deliver the drug to pancreatic cancer cells while avoiding clearance by macrophages. In certain embodiments, the drug comprises a small molecule, a protein, a peptide, a mRNA, a miRNA, a RNAi, an oligonucleotide, or a combination thereof. In certain embodiments, the drug is a chemotherapeutic agent. In certain embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a method for making exosomes displaying a peptide, the method comprising modifying a first CD9 protein with a first peptide to form a first modified CD9 protein; transfecting HEK 293 cells with a vector expressing the first modified CD9 protein; harvesting exosomes from the culture medium of transfected cells; and purifying the harvested exosomes to obtain exosomes expressing the first peptide. In certain embodiments, the method further comprises modifying a second CD9 protein with a second peptide to form a second modified CD9 protein, and the step of transfecting the HEK 293 cells with a vector expressing the second modified CD9 protein, wherein the obtained exosomes display the second peptide. In certain embodiments, the method further comprises loading a drug into the obtained exosomes.

Further provided is a smart exosome comprising a first peptide incorporated into a first CD9 protein and displayed on an exosomal surface, wherein the first peptide provides a homing functionality to the smart exosome; and a second peptide incorporated into a second CD9 protein and displayed on the exosomal surface, wherein the second peptide provides an evasion functionality to the smart exosome. In certain embodiments, the first peptide comprises RGD. In certain embodiments, the second peptide comprises CD47$^{p110-130}$. In certain embodiments, the first peptide comprises RGD and the second peptide comprises CD47$^{p110-130}$. In certain embodiments, the smart exosome further comprises a drug encapsulated therein. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a smart exosome comprising a first CD9 protein having an extracellular loop with an RGD incorporated therein at a E174 residue; and a second CD9 protein having an extracellular loop with a CD47$^{p110-130}$ peptide incorporated therein at a E174 residue or at a V178 residue. In certain embodiments, the smart exosome further comprises a drug encapsulated therein. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a composition comprising an exosome that co-expresses RGD and CD47$^{p110-130}$ at a surface. In certain embodiments, the exosome further comprises a drug encapsulated therein. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a composition comprising an exosome that co-expresses CD9-RGD and CD9-CD47$^{p110-130}$. In certain embodiments, the exosome further comprises a drug encapsulated therein. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a method for making a smart exosome, the method comprising incorporating a first peptide into a first extracellular loop of a first CD9 protein of an exosome, wherein the first peptide binds specifically to a protein expressed by a desired target; and incorporating a second peptide into a second extracellular loop of a second CD9 protein of the exosome, wherein the second peptide is recognized by macrophages to allow the smart exosome to evade phagocytosis by macrophages. In certain embodiments, the method further comprises encapsulating a drug into the smart exosome. In particular embodiments, the drug comprises a small molecule, a protein, a peptide, a mRNA, a miRNA, a RNAi, an oligonucleotide, or a combination thereof. In particular embodiments, the drug is a chemotherapeutic agent. In particular embodiments, the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

Further provided is a kit comprising a first container housing exosomes, wherein the exosomes comprise a peptide incorporated into a CD9 protein; and a second container housing a drug.

Further provided is a kit comprising a first container housing cells; and a second container housing a CD9 protein modified to include a peptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates the smart exosome, and FIG. 1B illustrates the smart exosome interacting with a macrophage and a PDAC cell.

FIG. 3G shows radiance of Exo$^{CD9-HA-RGD}$ compared to Exo$^{Cntrl}$ in a PDCL5 tumor.

FIG. 4D shows relative binding activity.

DETAILED DESCRIPTION

Figure 1A:
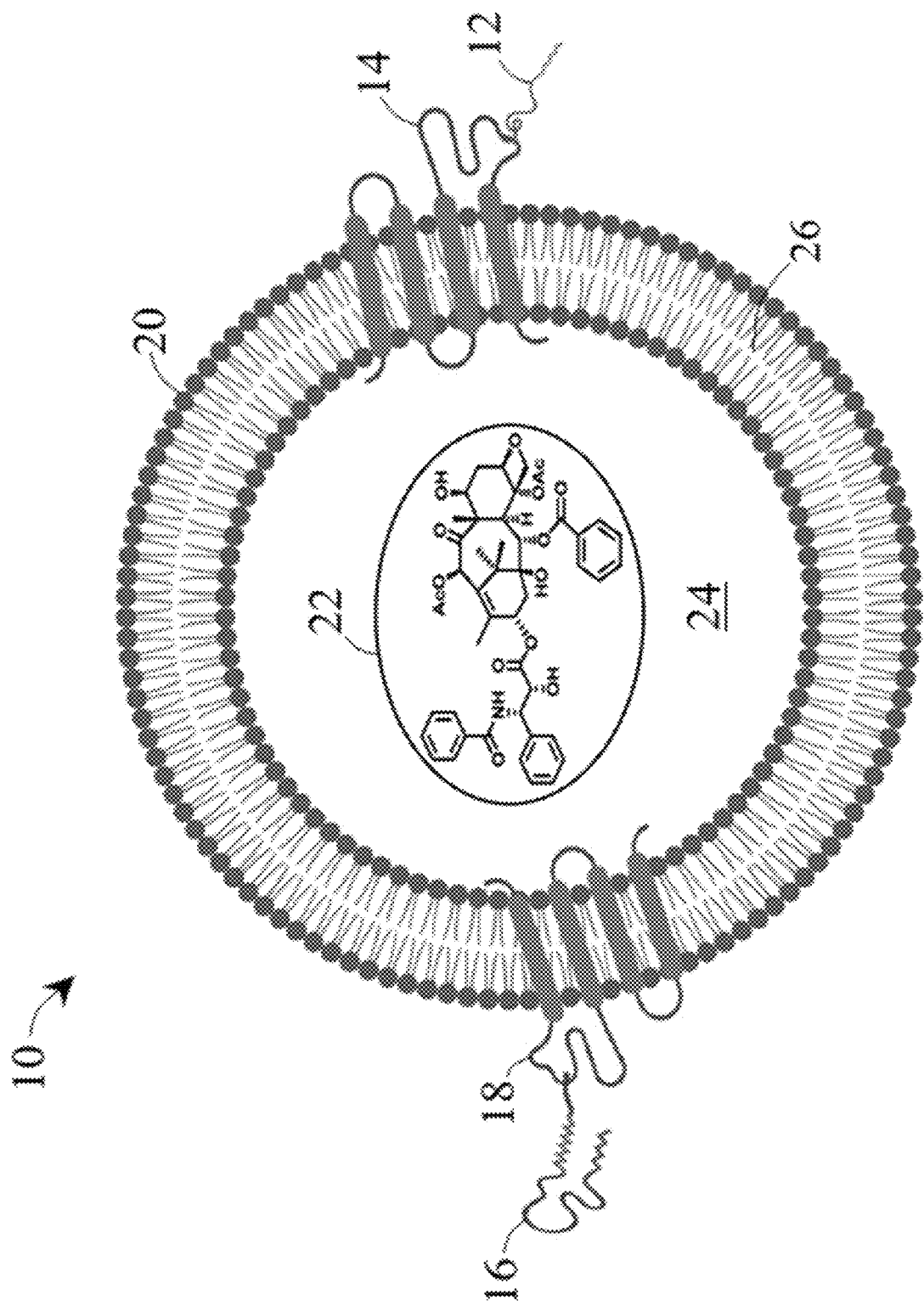
FIGS. 1A-1B: Illustrations of a smart exosome in accordance with the present disclosure that displays both RGD and CD47$^{p110-130}$ through CD9 engineering to enhance PDAC tumor uptake and prevent phagocytosis by macrophages.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided are exosomes useful for delivering drugs to desired targets. The exosomes include engineered CD9 proteins which display one or more peptides on the surfaces of the exosomes. CD9 is a unique, editable membrane protein that is enriched in exosomes. While certain sites on the tetraspanin CD63 are to known to be able to allow the integration of fluorescent fusion proteins on the extravesicular side of the exosomal membrane, there has been a lack of CD9 engineering for peptide exosomal surface display. In accordance with the present disclosure, CD9 is a highly efficient and stable membrane protein carrier to display peptides on exosomal surfaces. In particular, the variable region of the large extracellular loop (LEL) of CD9 shows marked conformational fluctuations and is therefore considered to mediate interactions with partner proteins. The CD9 LEL is a suitable place to incorporate one or more peptides for expression of the peptide(s) on exosomal surfaces.

In some embodiments, the exosomes include a first peptide incorporated into a first CD9 protein, and a second peptide incorporated into a second CD9 protein, where the first peptide provides a homing functionality and the second peptide provides an evasion functionality. Such exosomes may be referred to herein as smart exosomes.

The homing functionality, when included, can direct the exosomes to a desired target by binding to proteins specific to the target. As a non-limiting example, the exosomes may incorporate the peptide RGD, or arginylglycylaspartic acid, in order to provide homing to PDAC tumor cells. RGD is a peptide responsible for cell adhesion to the extracellular matrix (ECM). The RGD peptide may be strictly the amino acids RGD, or in the form of a longer amino acid sequence that includes the RGD sequence such as, but not limited to, CDCRGDCFC (SEQ ID NO: 1). The examples herein demonstrate that exosomes expressing the RGD sequence exhibit homing to PDAC tumor cells.

The evasion functionality, when included, can allow for the exosomes to significantly evade phagocytosis by the spleen and liver. As a non-limiting example, the exosomes may incorporate the minimal self-peptide CD47$^{p110-130}$ onto exosomal surfaces. The examples herein demonstrate that it is feasible to display CD47$^{p110-130}$ on the surface of exosomes via integration into CD9 (Exo$^{CD9-CD47p110-130}$). The CD47$^{p110-130}$ peptide is a portion of the CD47 protein, between residues G110 and K130, having the amino acid sequence of GNYTCEVTELTREGETIIELK (SEQ ID NO: 2). It is demonstrated in the examples herein that overexpression of CD47 on exosomes delays macrophage-mediated clearance of nanoparticles. CD47 recognizes the receptor or macrophage, to avoid being eaten. Exosomes engineered to express CD47 or a portion thereof can thus significantly evade phagocytosis by the liver and spleen. In embodiments wherein the desired target of the exosomes is a PDAC tumor, this allows for enhanced PDAC tumor targeting.

Figure 1B:
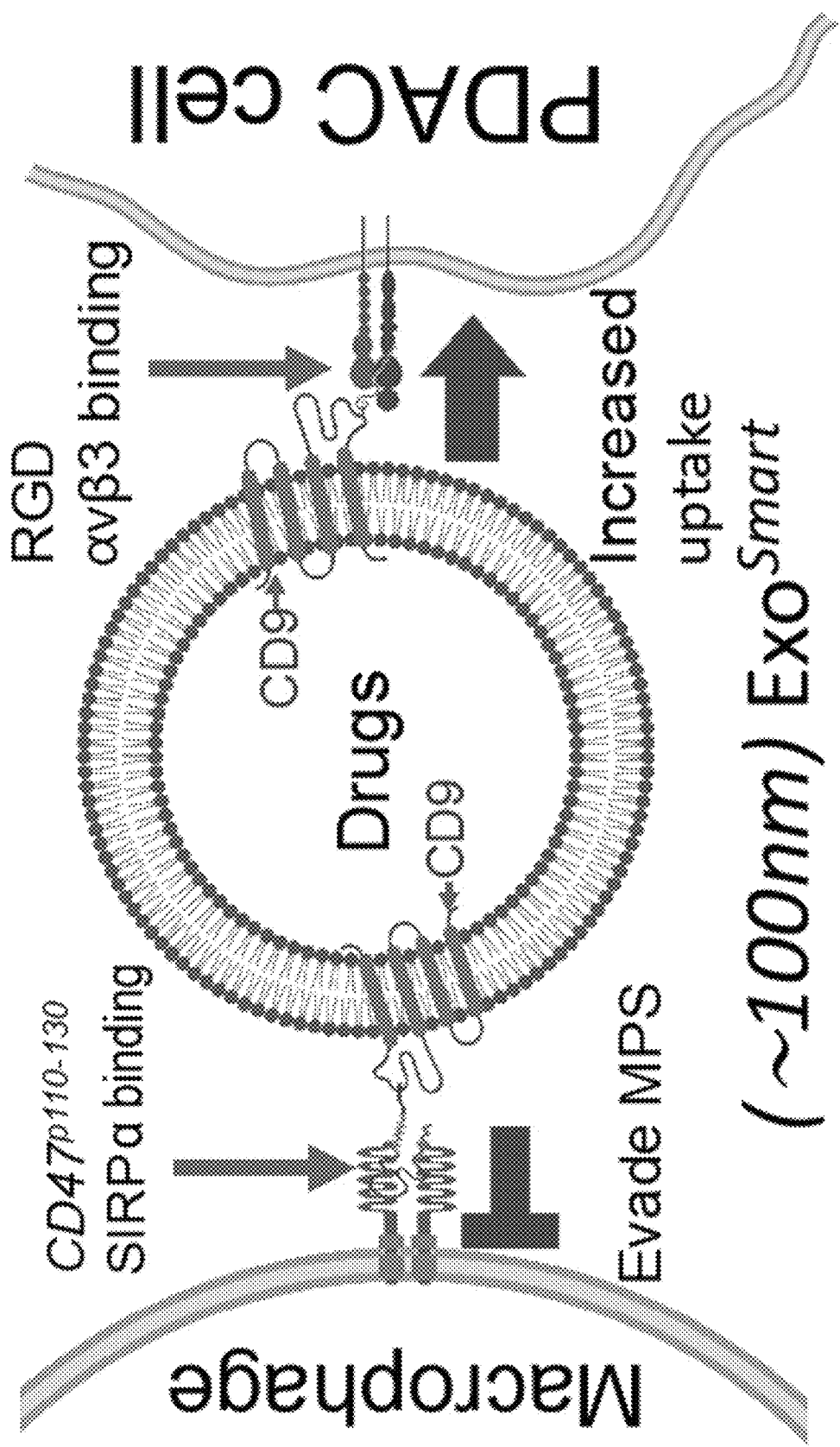

A non-limiting example smart exosome is depicted in FIGS. 1A-1B. Referring now to FIG. 1A, an example smart exosome 10 includes the RGD peptide 12 incorporated into a first CD9 protein 14 and the CD47$^{p110-130}$ peptide 16 incorporated into a second CD9 protein 18, so as to co-express the RGD peptide 12 and the CD47$^{p110-130}$ peptide 16 on the exosomal surface 20 to home the exosome 10 to PDAC tumor cells and to evade phagocytosis clearance by macrophages. CD9 is the protein utilized for this purpose because CD9 is enriched in exosomes and can display peptides on the surface 20. One or more drugs 22 can be encapsulated within the core 24 of the smart exosome 10, surrounded by the lipid membrane bilayer 26. (For illustration purposes, the structure of paclitaxel is depicted as the drug 22 in FIG. 1A.) This example embodiment of the smart exosome 10, which co-expresses both the RGD peptide 12 and the CD47$^{p110-130}$ peptide 16, may be referred to herein as Exo$^{CD9-RGD}$/CD9-CD47$^{p110-130}$ or Exo$^{Smart}$. The examples herein demonstrate that dual display of RGD and $CD47^{p110-130}$ allows the exosomes to evade phagocytosis of macrophages while simultaneously homing to pancreatic tumor cells specifically. The examples herein utilize a xenograft pancreatic cancer tumor model in mice to demonstrate that the smart exosomes are a useful pancreatic cancer targeted delivery system.

Exosomes in general are nanosized membrane vesicles that are secreted by most types of cells, and are known to transfer DNA, RNA, and proteins between cells, and to facilitate intercellular communication. Exosomes are generally composed of a lipid membrane bilayer structure that surrounds a hydrophilic core. The exosomes usable in accordance with the present disclosure may be harvested from the culture medium of CD9-transfected cells, such as $CD9\_E174\text{-}CD47^{p110-130-Flag}$ transfected HEK 293 cells. Methods such as ultracentrifugation can be used to harvest the exosomes, and the exosomes can be purified by a suitable process such as gel-filtration chromatography or size-exclusion chromatography. Thus, a method for making an exosome in accordance with the present disclosure may include the steps of modifying a CD9 protein with a peptide to form a modified CD9 protein, transfecting cells with a vector expressing the modified CD9 protein, and harvesting exosomes from the culture medium of the transfected cells. The method may further include purifying the harvested exosomes. In some embodiments, the method includes modifying a second CD9 protein with a second peptide to form a second modified CD9 protein, and transfecting the cells with both vectors expressing modified CD9 proteins, before harvesting exosomes from the culture medium of the transfected cells.

Though not necessary, any of the peptides incorporated into the CD9 proteins as described herein may be labeled or tagged. Non-limiting examples of suitable tags for the peptides are biotin or biotin variant tags, carboxylase carrier protein (BCCP) tags, myc-tags, calmodulin-tags. FLAG-tags, hemagglutinin (HA)-tags, polyhistidine tags (also referred to as histidine tags or His-tags), maltose binding proteim (MBP)-tags, nus-tags, glutathione-S-transferase (GST)-tags, green fluorescent protein (GFP)-tags, thioredoxin-tags, S-tags, Softags, stre-tags, biotin ligase tags, FAsH tags, V5 tags, and SBP-tags. However, other tags are possible and encompassed within the scope of the present disclosure. A tag may, for instance, allow the exosomes to be tracked in vivo by bioluminescence or fluorescence.

In other embodiments, provided herein are exosomes having only one peptide incorporated onto exosomal surfaces through CD9 engineering. Thus, it is not strictly necessary to incorporate two different peptides into CD9 proteins on an exosome, and such exosomes are encompassed within the scope of the present disclosure. Moreover, it is understood that more than one peptide may be incorporated into the same CD9 protein, and such embodiments are encompassed within the scope of the present disclosure. Furthermore, though embodiments having one or two peptides incorporated into CD9 proteins are described for example purposes, it is understood that the present disclosure is not limited to only one or more peptides being expressed on the surface through CD9 proteins; rather, it is understood that more than two CD9 proteins may be modified with more than two peptides, exosomes can be harvested following transfection of cells with such vectors expressing modified CD9 proteins so as to obtain exosomes which include more than two peptides expressed on the surface in modified CD9 proteins, and such embodiments are encompassed within the scope of the present disclosure.

The exosomes can be loaded with a wide variety of drugs such as, but not limited to, small molecules, proteins, peptides, mRNAs, miRNAs, RNAis, oligonucleotides, and combinations thereof. In some embodiments, the smart exosomes are loaded with one or more chemotherapeutic agents. In one non-limiting example, the smart exosomes include paclitaxel. Non-limiting examples of drugs that can be encapsulated into, and delivered by, the exosomes are paclitaxel, 5-fluorouracil, abraxane (paclitaxel albumin-stabilized nanoparticle formulation), afinitor (everolimus), erlotinib hydrochloride, everolimus, gemcitabine hydrochloride, oxaliplatin (eloxatin), capecitabine (xeloda), cisplatin, irinotecan (camptosar), colinic acid (leucovorin), folfox (folinic acid, 5-fluorouracil, and oxaliplatin), folfirinox (folinic acid, 5-fluorouracil, irinotecan, and oxaliplatin), nab-paclitaxel with gemcitabine, metformin, digoxin, simvastatin, and combinations thereof.

To load an exosome with a drug, the drug can simply be mixed or incubated with the exosomes for a sufficient time for the drugs to diffuse into the exosomes and be encapsulated thereby. Alternatively, the cells used to create the exosomes may be treated with a drug prior to harvesting the exosomes, and such cells may then secrete exosomes already loaded with the drug. However, other methods of incorporated drugs into the exosomes are possible and encompassed within the scope of the present disclosure. The exosomes may then be used to deliver the drug(s) to a desired target, which may be aided by a homing ability of a peptide incorporated into a CD9 protein of the exosomes as described above. Once at the target, the drug is released over time from the exosomes.

The exosomes described herein are advantageous for delivering therapeutic agents to treat diseases with targeted precision, and for evading clearance by macrophages. As shown in the examples herein, examples of the engineered exosomes can deliver drugs, home to PDAC tumor cells, and evade phagocytosis by the spleen and liver. Thus, to overcome the obstacles of active cellular targeting and clearance by the MPS, provided herein are genetically engineered smart exosomes that enhance cellular targeting and prevents the phagocytosis from MPS, and are capable of delivering drugs.

Pharmaceutical compositions of the present disclosure may comprise an effective amount of an exosome described herein, such as a smart exosome loaded with a drug, and/or additional agents, dissolved or dispersed in a pharmaceutically acceptable carrier. The preparation of a pharmaceutical composition will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515, and 5,399,363 are each specifically incorporated herein by reference in their entirety).

Solutions of the compositions disclosed may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In some cases, it may be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

The compositions and methods described herein may also be made available via a kit containing one or more key components. A non-limiting example of such a kit comprises a drug and exosomes in separate containers, where the exosomes comprise a peptide incorporated into a CD9 protein, and where the containers may or may not be present in a combined configuration. Many other kits are possible, such as kits comprising cells and a CD9 protein modified to include a peptide in separate containers. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

These examples describe the development of an exosome-based delivery system in which engineered exosomes can simultaneously target PDAC tumor cells and escape phagocyte immune clearance. Instead of individually targeting these activities, the engineered dual-function exosomes, an entropy-favored system, can achieve highly effective PDAC targeting simultaneously with minimal MPS clearance. These examples demonstrate that a smart exosome can be generated by engineering the CD9 surface proteins of exosomes to display the tumor homing peptide RGD (Arg-Gly-Asp) and the minimal self-peptide $CD47^{p110-130}$ (CD47 peptide between G110-K130) on the exosomal surface (FIG. 1B).

RGD peptide is a ligand of $\alpha v\beta 3$ that is widely expressed in various cancers including PDAC and is associated with growth, survival, invasion, and metastasis of different cancer cells. The peptide has been studied for cancer targeted therapies and imaging. On the other hand, CD47 has been shown to serve as a "don't eat me" signal to macrophages in order to evade phagocytosis, thereby minimizing MPS clearance. $CD47^{p110-130}$ is believed to play a critical role in mediating the CD47 interaction with single-regulatory protein alpha (SIRPα; CD172A). CD9, a 21-24 kDa member of the tetraspanin protein family, is enriched on exosome membrane and defined as an exosome biomarker. The N-terminus of CD9 engineering has been used to successfully load cargo proteins into newly generated exosomes, however, there has previously been no report of CD9 engineering for peptide exosomal surface display. The variable region of the large extracellular loop (CD9 LEL) shows marked conformational fluctuations which is important for engineering peptide display, and the E174 residue at CD9 LEL, a critical site for sperm-egg fusion and CD9 binding to its counterpart, is believed to mediate interactions.

Example I

CD9 Engineering for Exosome RGD Display

Figure 2A:
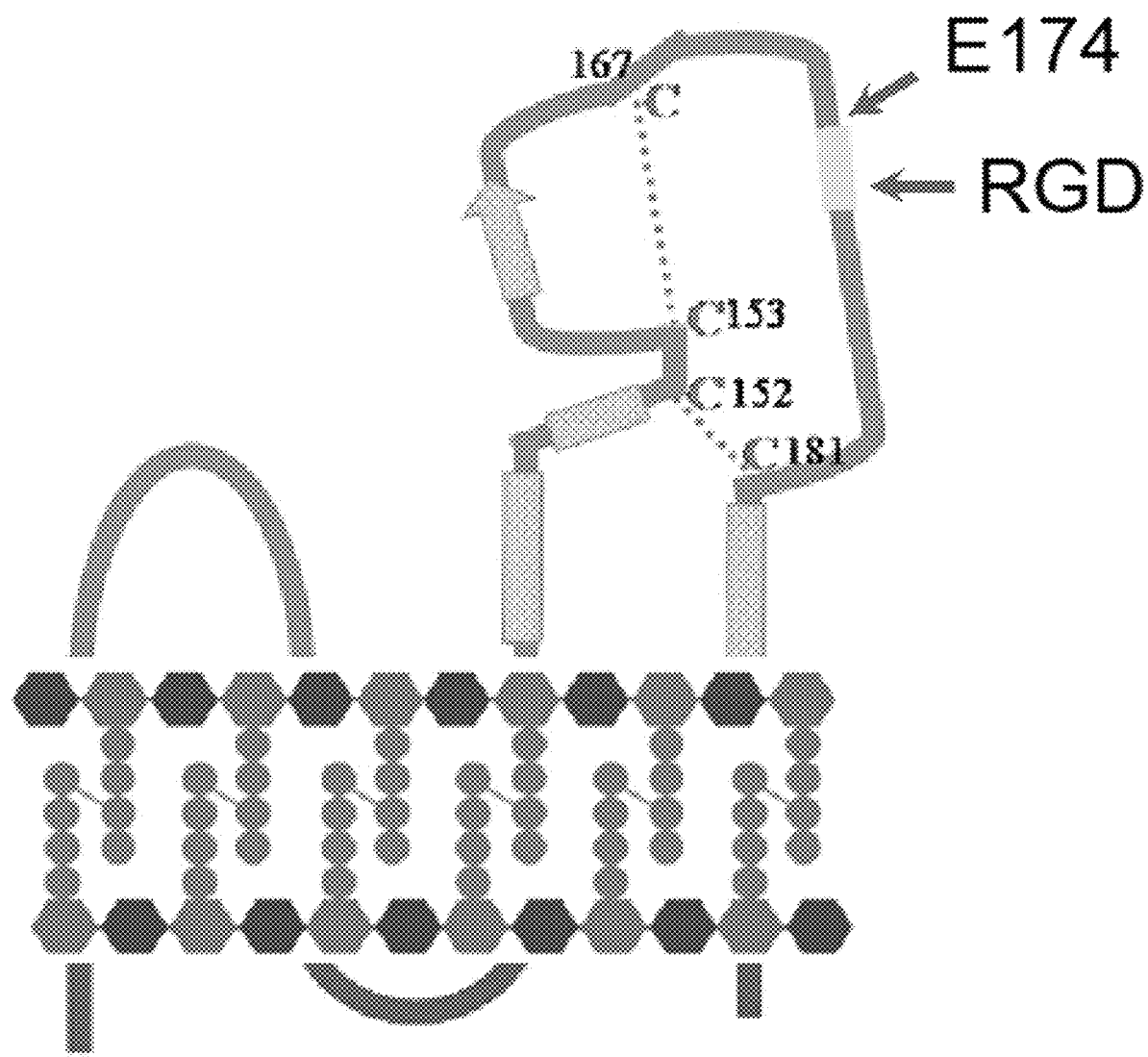
FIGS. 2A-2G: CD9 engineering. Insertion of RGD into CD9 LEL at E174 (FIG. 2A) abolished the anti-CD9 antibody binding to CD9 protein (FIG. 2B, red box) via western blot, but enhanced the CD9 binding to αvβ3 protein (FIG. 2C, red box) via ELISA assay. Flow cytometry detected HA expression on Exo$^{CD9-HA-RGD}$ (FIG. 2D) but not Exo$^{CD9-RGD}$ (FIG. 2E) with quantification (FIG. 2F). Exo$^{CD9-HA-RGD}$ had similar binding affinity to αvβ3 as compared to Exo$^{CD9-RGD}$ as determined by ELISA (FIG. 2G).
Figure 2B:
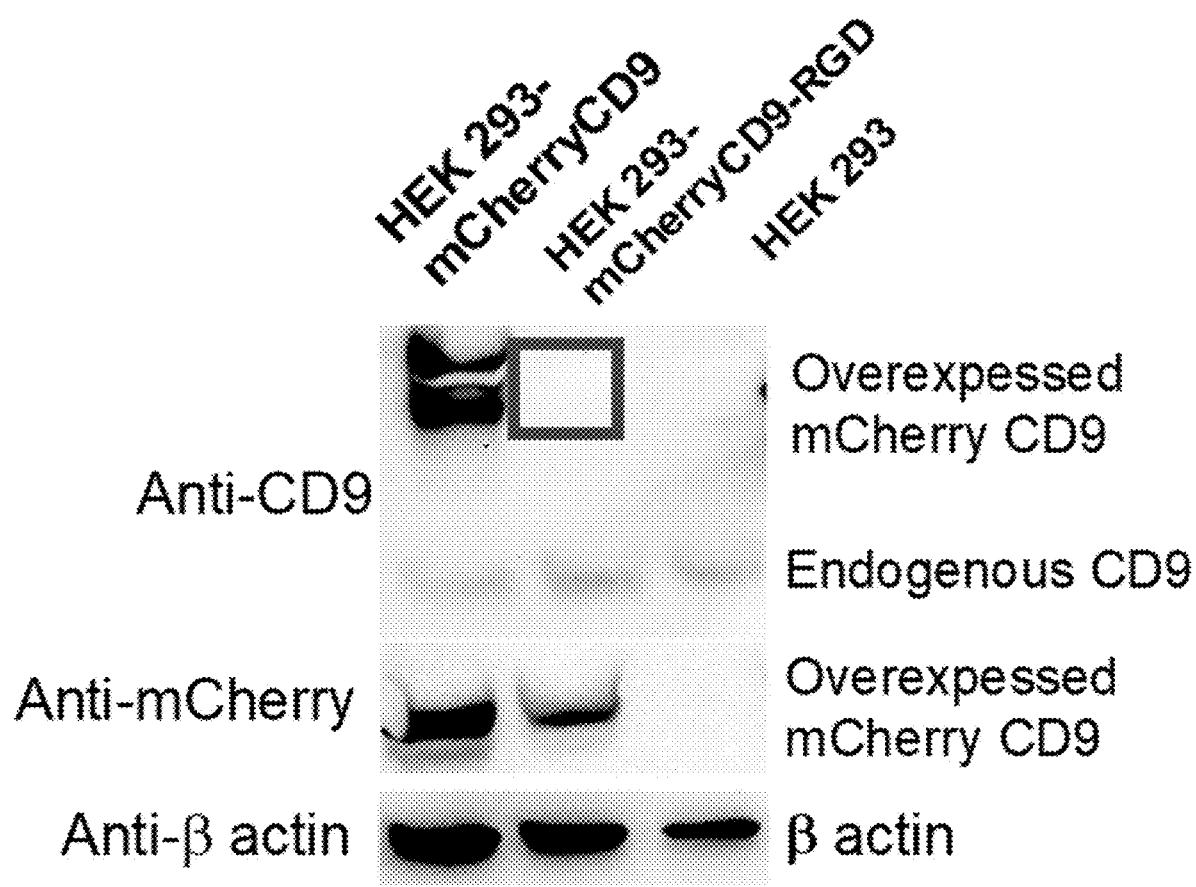
Figure 2C:
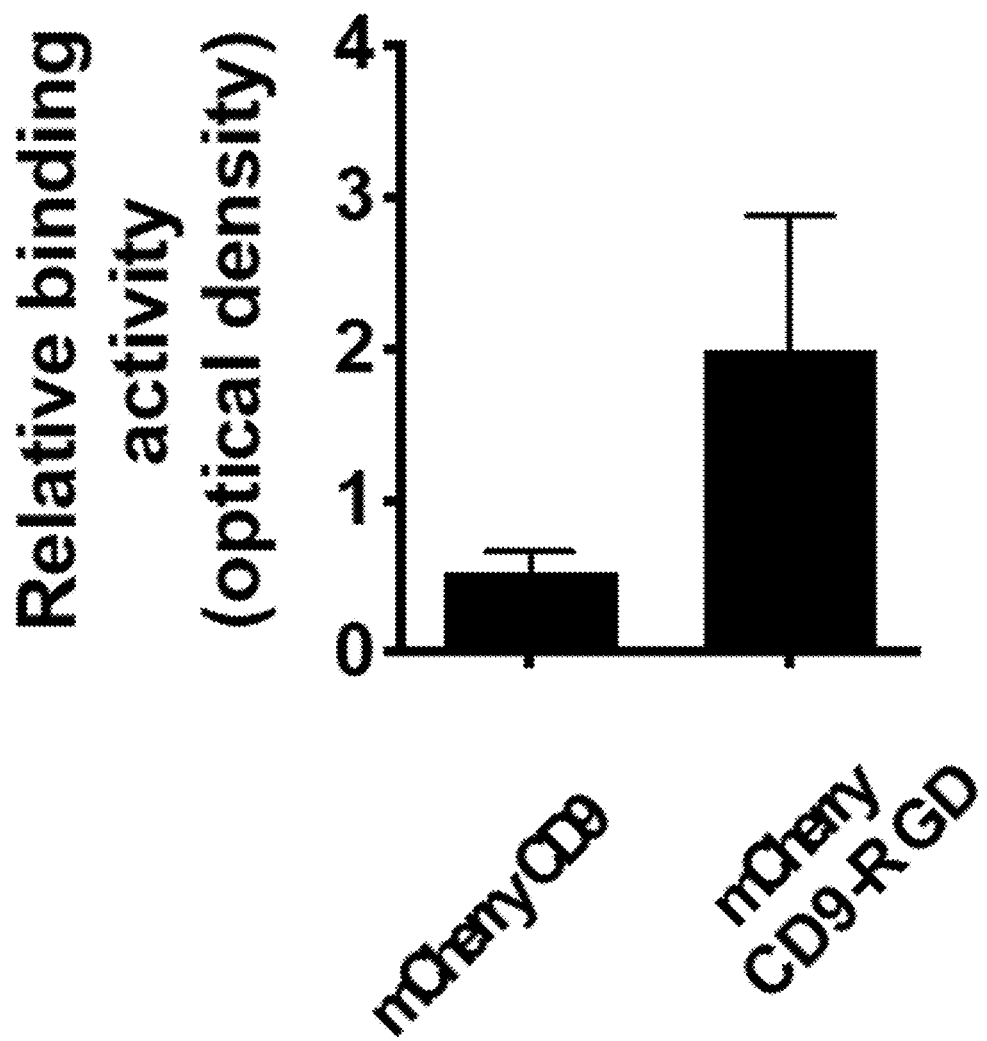

Insertion of RGD into CD9 LEL maintained normal expression of CD9 on HEK 293 cells but altered its innate binding ability. mCherry-CD9-RGD expression vector was constructed by inserting an RGD sequence into CD9's amino acid sequence between E174 and T175 (FIG. 2A). The mCherry-CD9 expression levels did not change when transfection of HEK 293 cells was performed. However, CD9-RGD failed to be detected by anti-CD9 antibody (CST Inc) that targets residues surrounding V178 of human CD9 (FIG. 2B; red box). Instead, it was found that mCherry-CD9-RDG protein strongly bound to $\alpha v\beta 3$ (FIG. 2C, red box), indicating that RGD display alters CD9 tropism toward RGD receptor, and indicating important translational ability of CD9 engineering to abolish binding to normal tissues and enhance binding to PDAC cells expressing $\alpha v\beta 3$. All experiments were repeated three times.

Figure 2D:
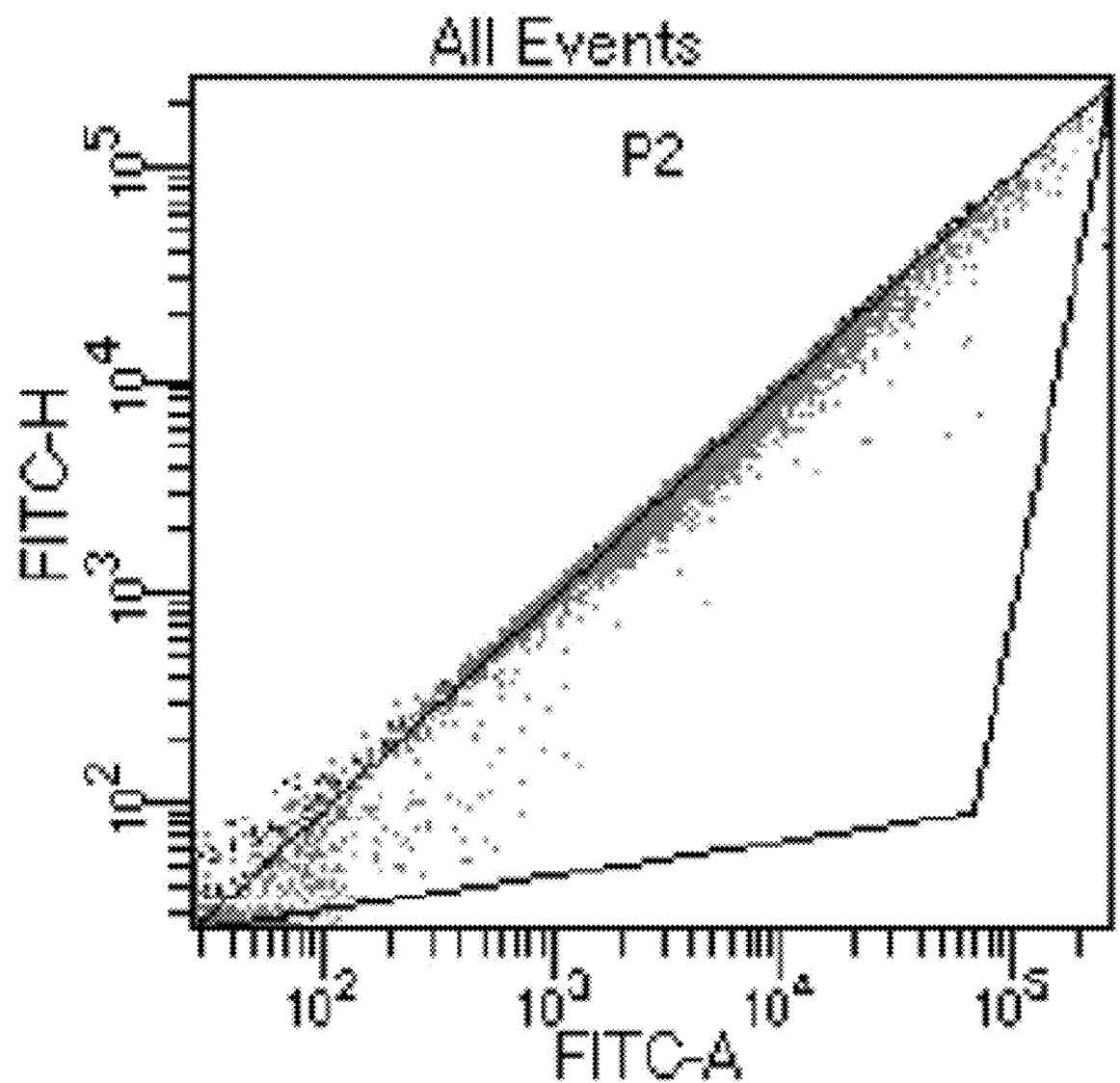
Figure 2E:
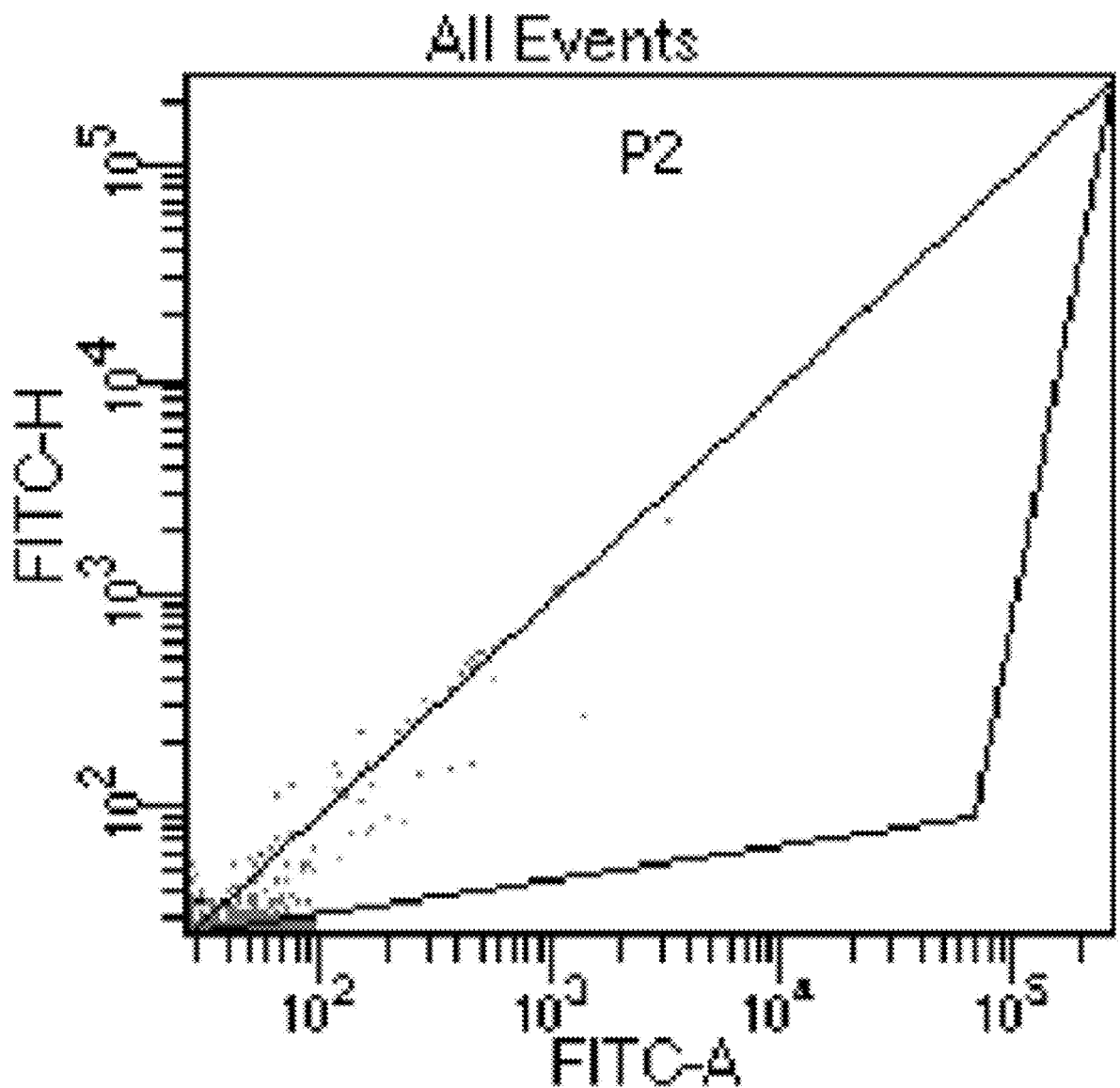
Figure 2F:
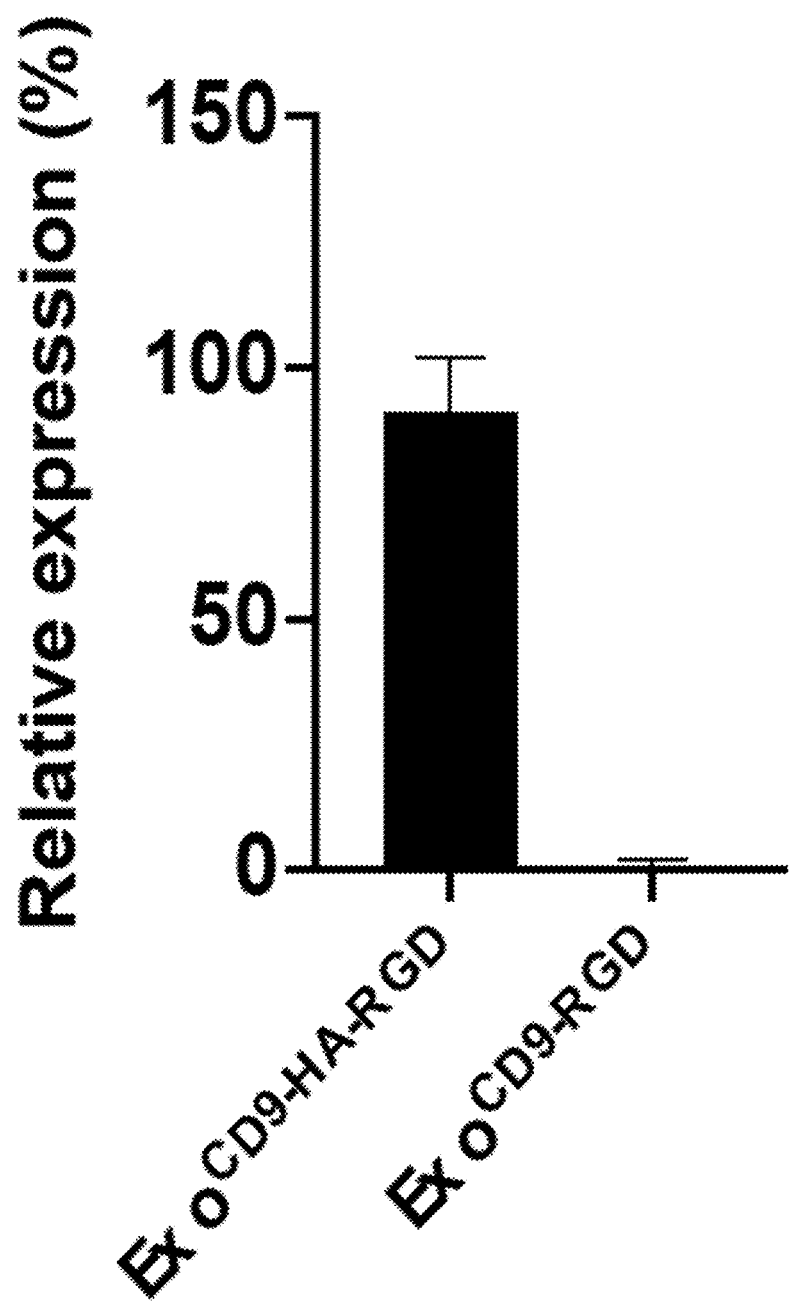
Figure 2G:
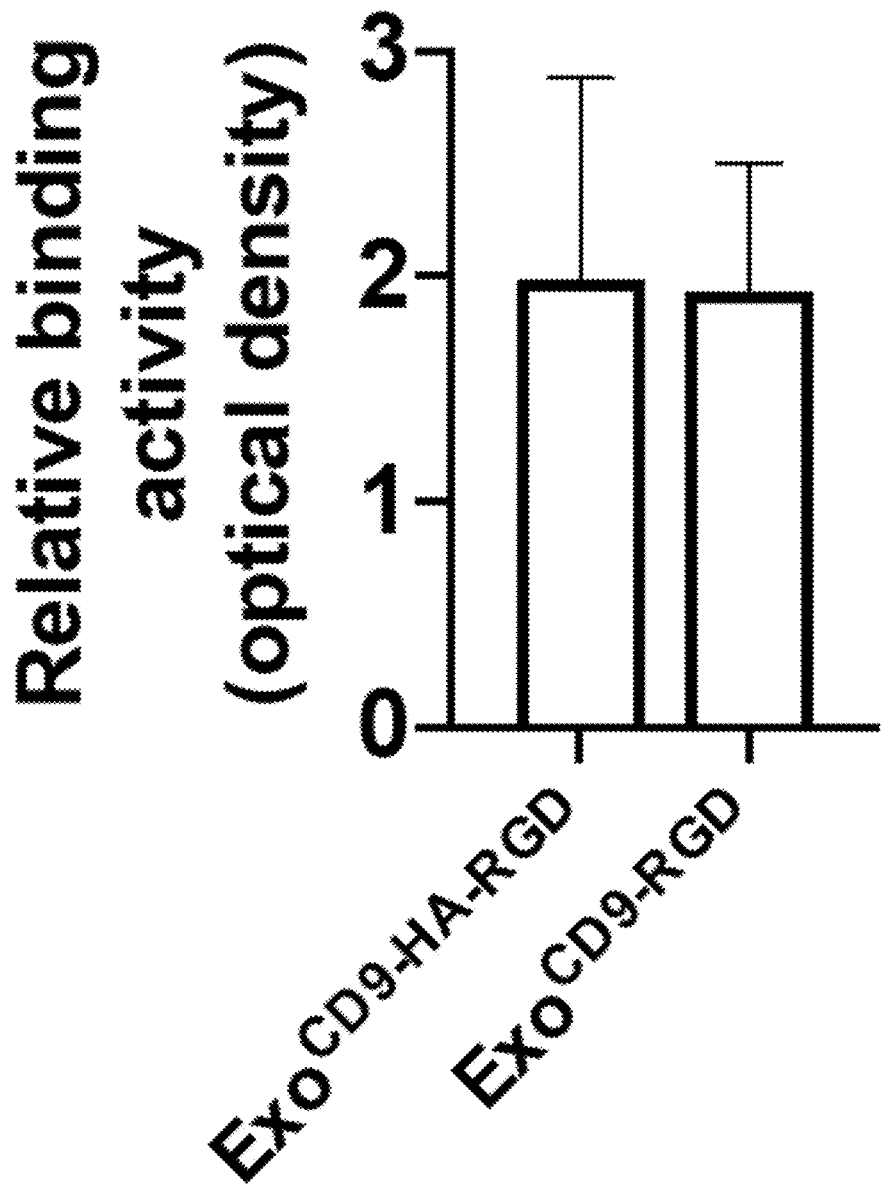

HA tag on RGD peptide did not interfere with RGD expression and function on exosome $pcDNA^{CD9\_E74-HA-RGD}$, $pcDNA^{CD9\_E174-RGD}$, and $pcDNA^{CD9}$ were generated. Exomes ($Exo^{CD9\_E174-HA-RGD}$ and $Exo^{CD9\_E174-RGD}$ and $Exo^{CD9}$) were obtained from culture media of transfected HEK 293 cells by ultracentrifugation (Optima LE-80K, Beckman) followed by Sepharose™ CL-4B size-exclusion chromatography (SEC). Flow cytometry assay analysis of HA tag demonstrated display of HA-RGD on $Exo^{CD9\_E174-HA-RGD}$ (FIG. 2D), but not $Exo^{CD9\_E174-RGD}$ (FIG. 2E), $p<0.05$ (FIG. 2F), while $Exo^{CD9\_E174-HA-RGD}$ had the same binding affinity as $Exo^{CD9\_E174-RGD}$ to $\alpha v\beta 3$ (experiments in triplicate) (FIG. 2G). These data indicate HA-tag on RGD has no impact on RGD's expression on an exosome and no impact on binding affinity to its receptor.

Figures 3A, 3B, 3C, 3D, 3E, 3F:
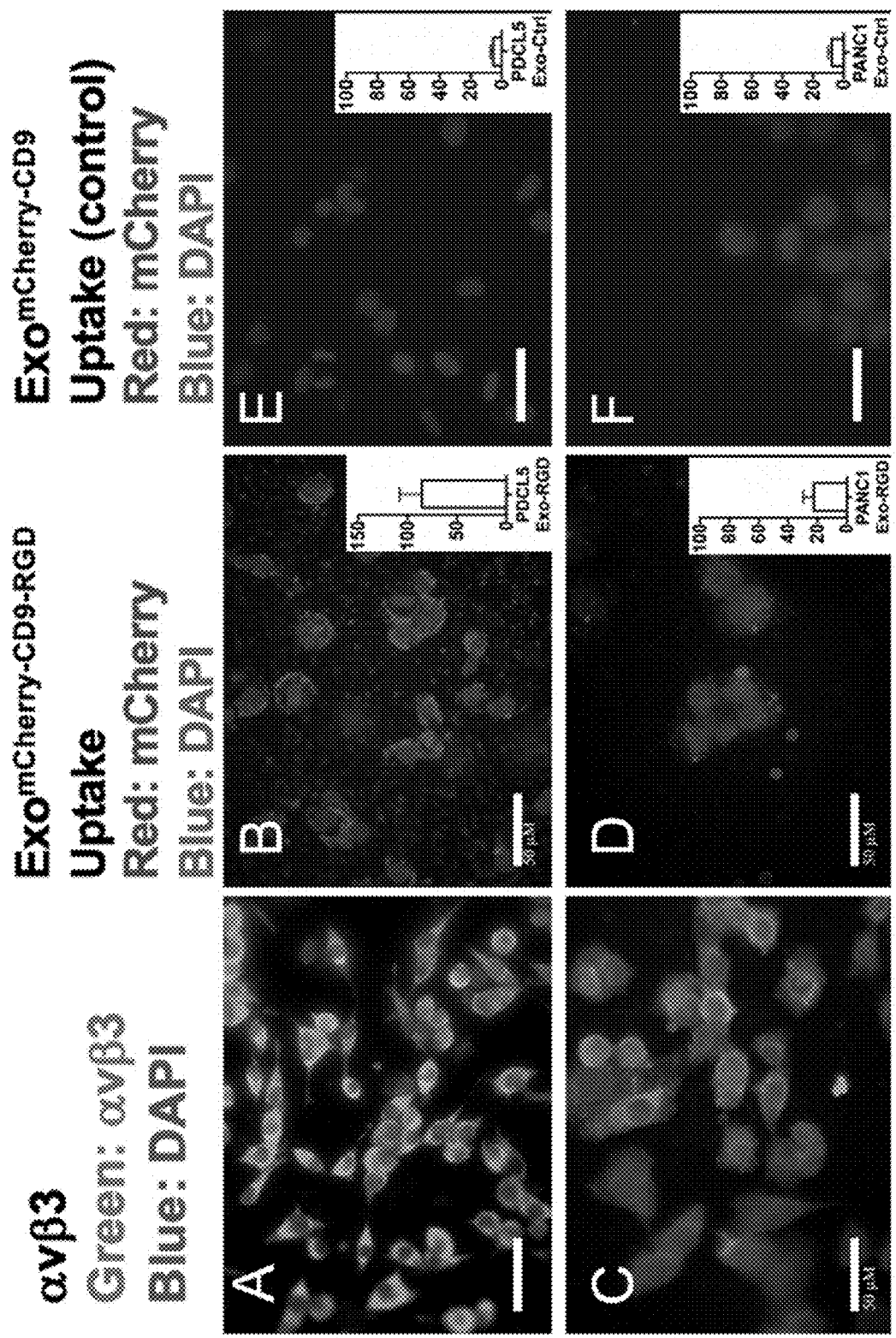
FIGS. 3A-3G: Exo$^{mCherry-CD9-RGD}$ uptake depends on the level of surface αvβ3 expression on recipient cells. Bar graphs represent quantification of exosome uptake (red color). Higher expression of αvβ3 in PDCL5 (FIG. 3A; green) resulted in higher exosome uptake (FIG. 3B; red). Lower expression αvβ3 in PANC1 (FIG. 3C; green) resulted in lower exosome uptake (FIG. 3D; red). Control exosomes lacking RGD had low uptake by PDAC and PDCL5 (FIGS. 3E & 3F, red). Scale bar=50 µm.
Figure 3G:
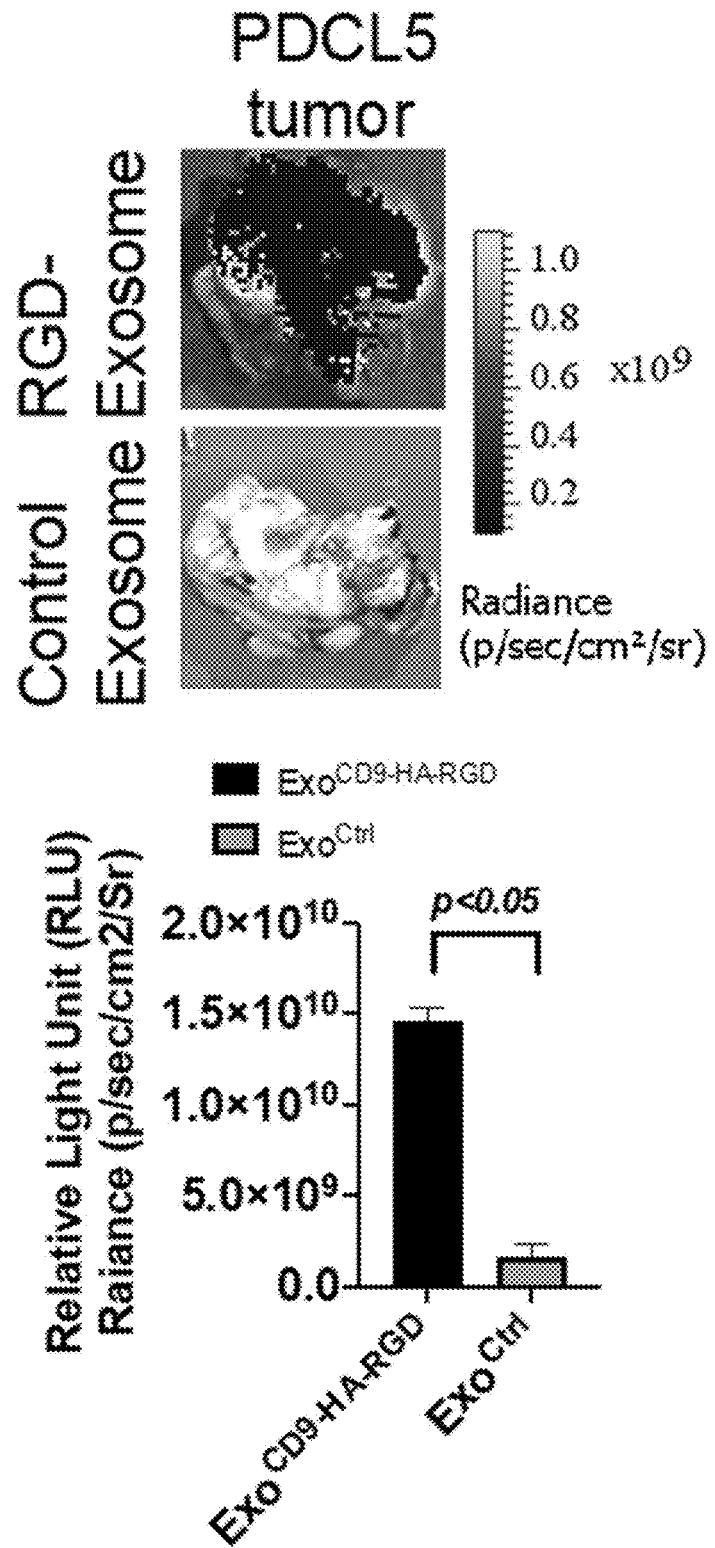

Exosome Uptake by PDAC Cells Changed Depending on RGD Insertion $Exo^{mCherry-CD9-RGD}$ and $Exo^{mCherry-CD9}$ were derived from HEK 293 cells. $2\times10^{10}$ exosomes per well were added to chamber slides with PANC1 or patient derived PDAC cell line (PDCL5). Images were captured using fluorescence microscope (Olympus IX70) after 24 h incubation. Integrin $\alpha v\beta 3$ expression was determined using anti-$\alpha v\beta 3$ antibody (CST) (experiments in triplicate). It was observed that $Exo^{mCherry-CD9-RGD}$ uptake relied on $\alpha v\beta 3$ expression on PDAC cells, where PDCL5 cells had higher expression of $\alpha v\beta 3$ (FIG. 3A; green) resulting in higher uptake of $Exo^{mCherry-CD9-RGD}$ (FIG. 3B; red), while PANC-1 cells had lower level of $\alpha v\beta 3$ expression (FIG. 3C panel; green) resulting in lower uptake of $Exo^{mCherry-CD9-RGD}$ (FIG. 3D; red). Quantitative analysis of exosome uptake (FIG. 3 bar graphs) revealed significant difference between them (p<0.05). Control exosomes lacking RGD (Exo$^{mCherry\text{-}CD9}$) demonstrated low uptake by PDAC and PDCL5 cells, irrespective of αvβ3 expression (FIGS. 3E & 3F; red). These data indicate that RDG display on the exosomal surface alter exosomal tropism toward αvβ3 expressing cells.

CD47 Mediates Low Clearance of Exosome by Liver and Spleen

Figure 4A:
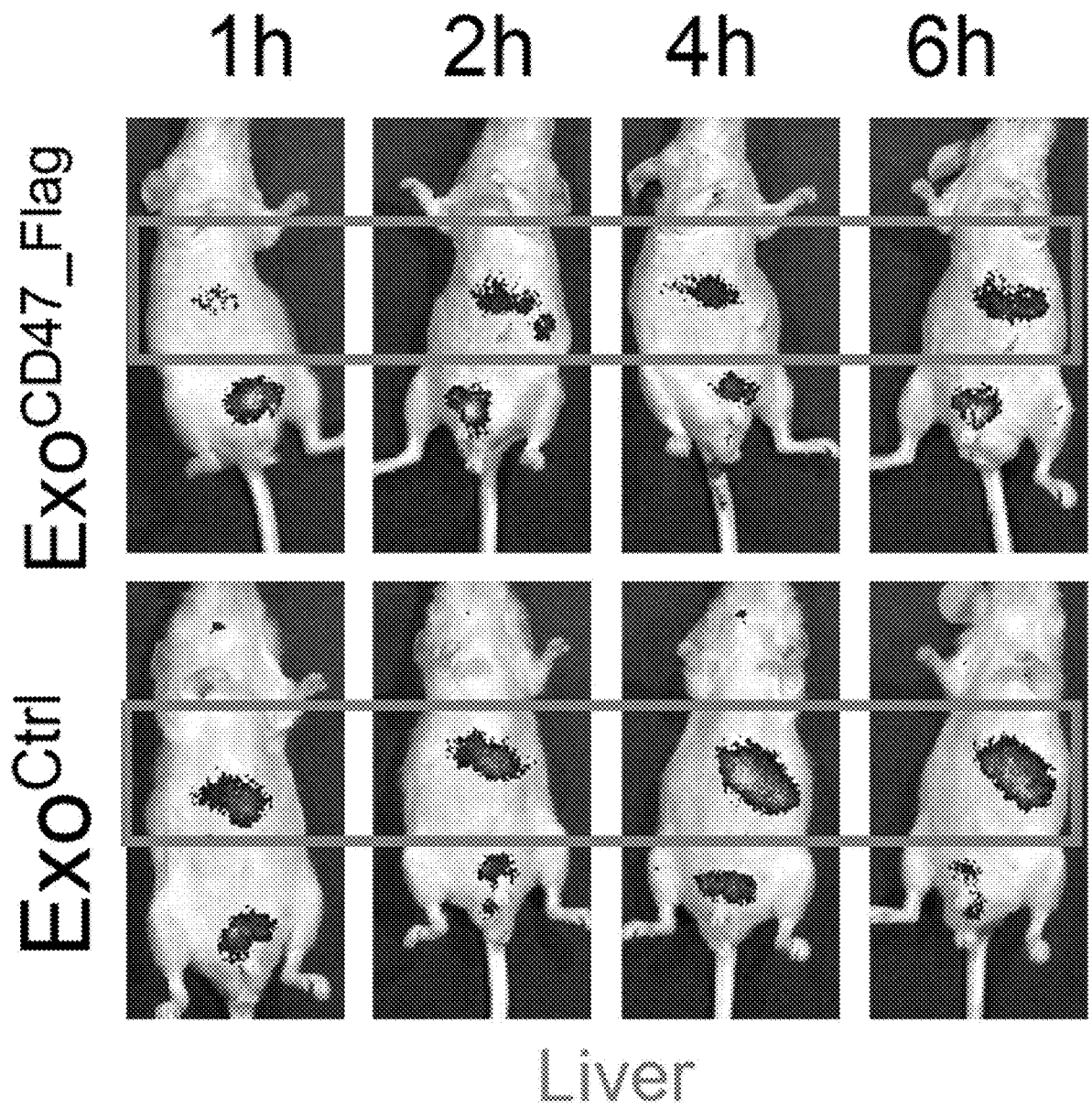
FIGS. 4A-4D: Systemic delivery 2×10$^{10}$ exosomal particles in mice showed lower retention of DiR stained exosomes in liver (FIG. 4A, blue box) and spleen (FIG. 4B; green box) in the Exo$^{CD47-Flag}$ group (top panel) compared to that of control (bottom panel), respectively. Organ NIR imaging of Exo$^{CD47\_Flag}$ group vs controls showed lower signals in liver (blue box, FIG. 4C) and spleen (green box, FIG. 4C). ELISA analysis of CD47$^{p110-130-Flag}$ showed high expression on CD47$^{p110-130-Flag}$ engineered exosomes.
Figure 4B:
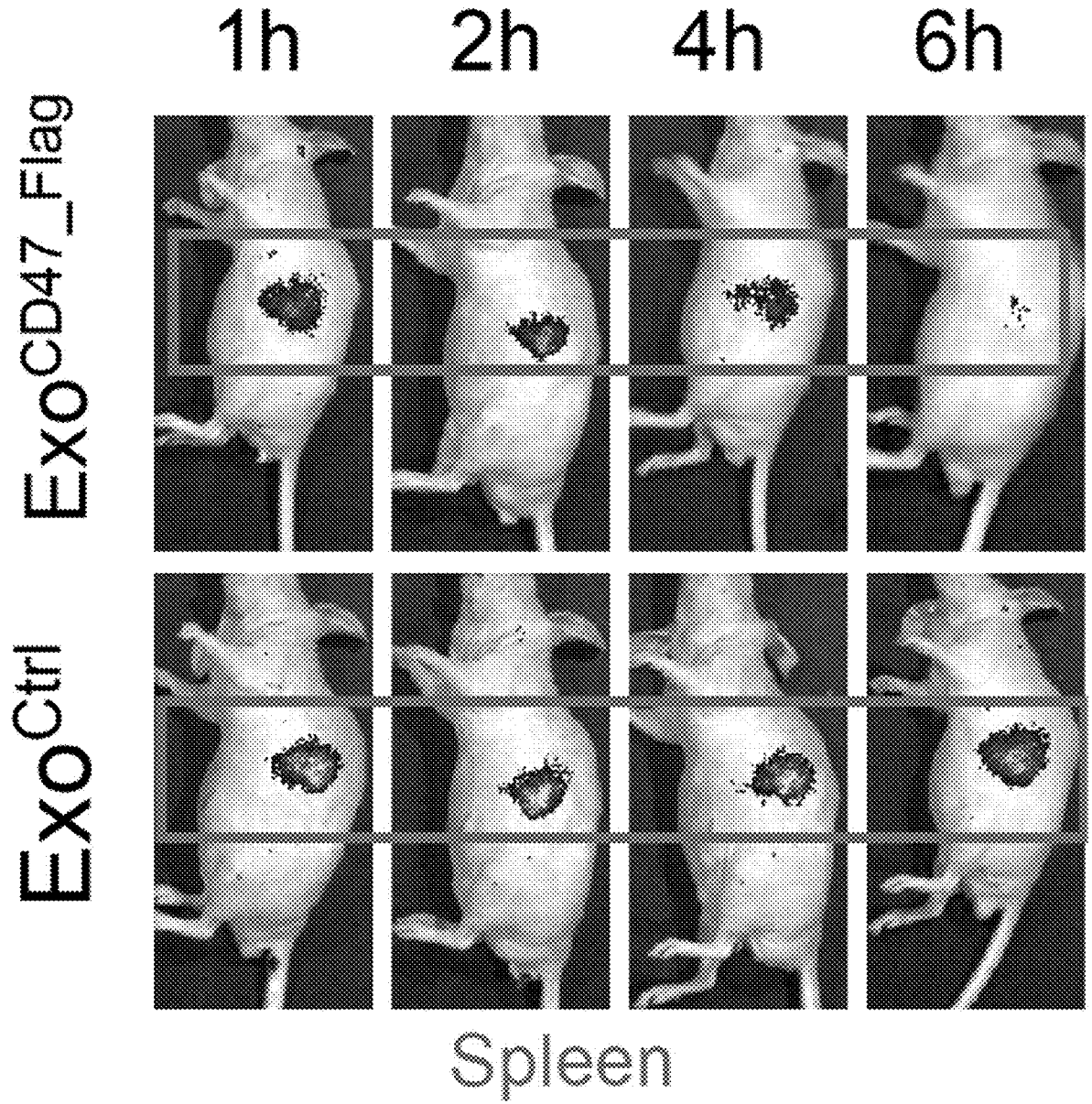
Figure 4C:
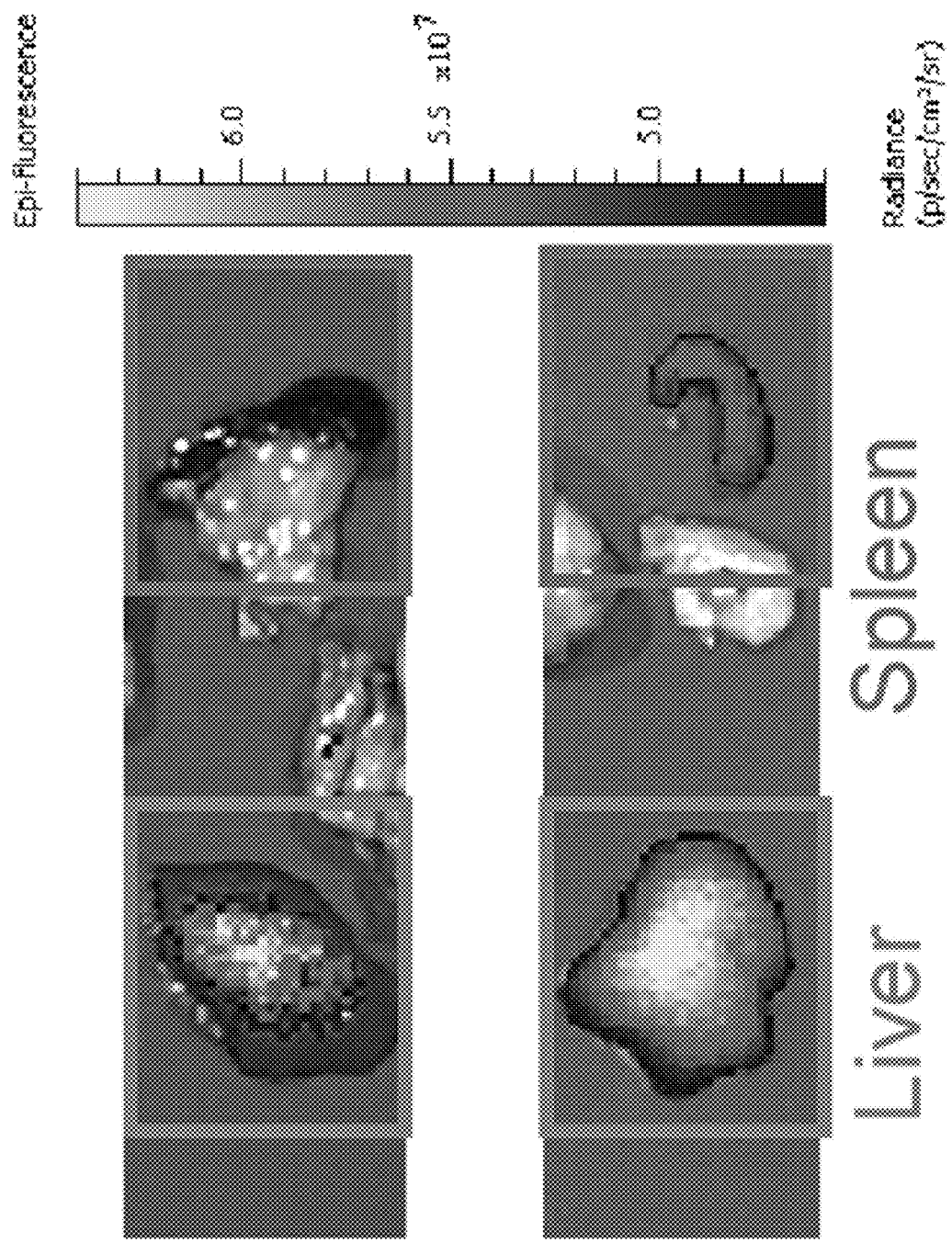

Exosome CD47-C-Flag (Exo$^{CD47\text{-}Flag}$) was derived from CD47-C-FLAG transfected HEK 293 cells and stained with lipid dye DiR (ThermoFisher Inc). 2×10$^{10}$ of exosomes/mouse (n=8) of control exosomes (Exo$^{Ctrl}$) and Exo$^{CD47\text{-}Flag}$ were IV injected into nude mice. The images were taken 1 h, 2 h, and 6 h after injection of DiR stained exosomes using an IVIS imager. The mice were sacrificed, and complete necroscopy was carried out 24 h after injection. Lower liver (FIG. 4A) and spleen (FIG. 4B) accumulation of DiR stained exosomes were found in the Exo$^{CD47\text{-}Flag}$ injected mouse group (top panel) as compared to the Exo$^{Ctrl}$ group (bottom panel). The organ imaging revealed that the Exo$^{CD47\text{-}Flag}$ group (FIG. 4C, top panel) had much lower exosome signals in liver and spleen (~2 times) than those of the control group (FIG. 4C, bottom panel). These data indicate that CD47 mediates low clearance of exosomes by the liver and spleen.

CD9$^{CD47p110\text{-}130}$ Efficiently Display on Exosomes

Figure 4D:
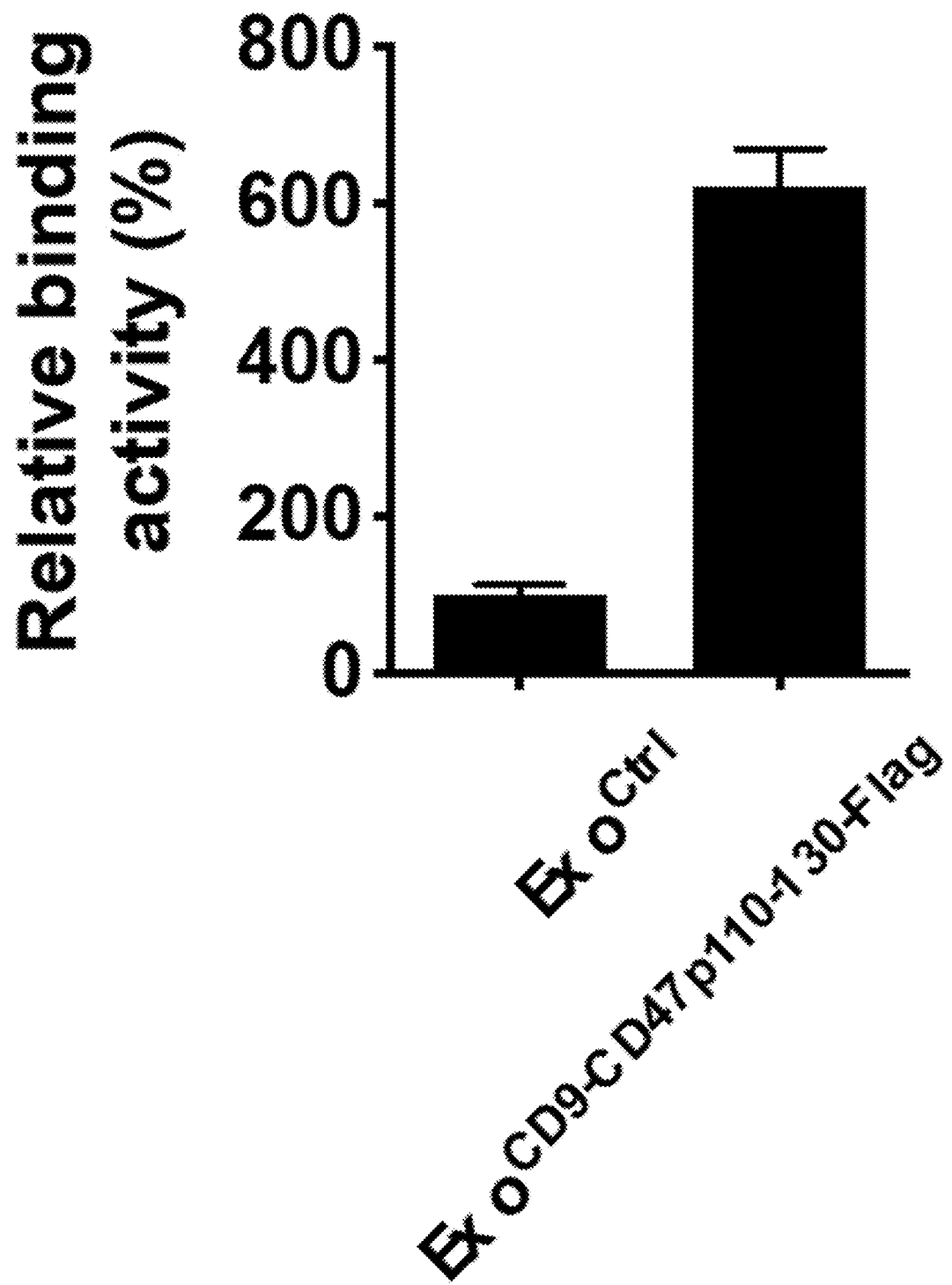

Exosomes that derived from CD9_E174-$^{CD47p110\text{-}130\text{-}Flag}$ transfected HEK 293 cells were harvested by ultracentrifugation and purified by SEC and subjected to ELISA assay. Flag peptide on Exo$^{CD9\text{-}CD47p110\text{-}130\text{-}Flag}$ measured up to 6 folds higher than that of control, demonstrating sufficient display of CD47$^{p110\text{-}130}$ on the exosome surface (FIG. 4D).

Figure 5A:
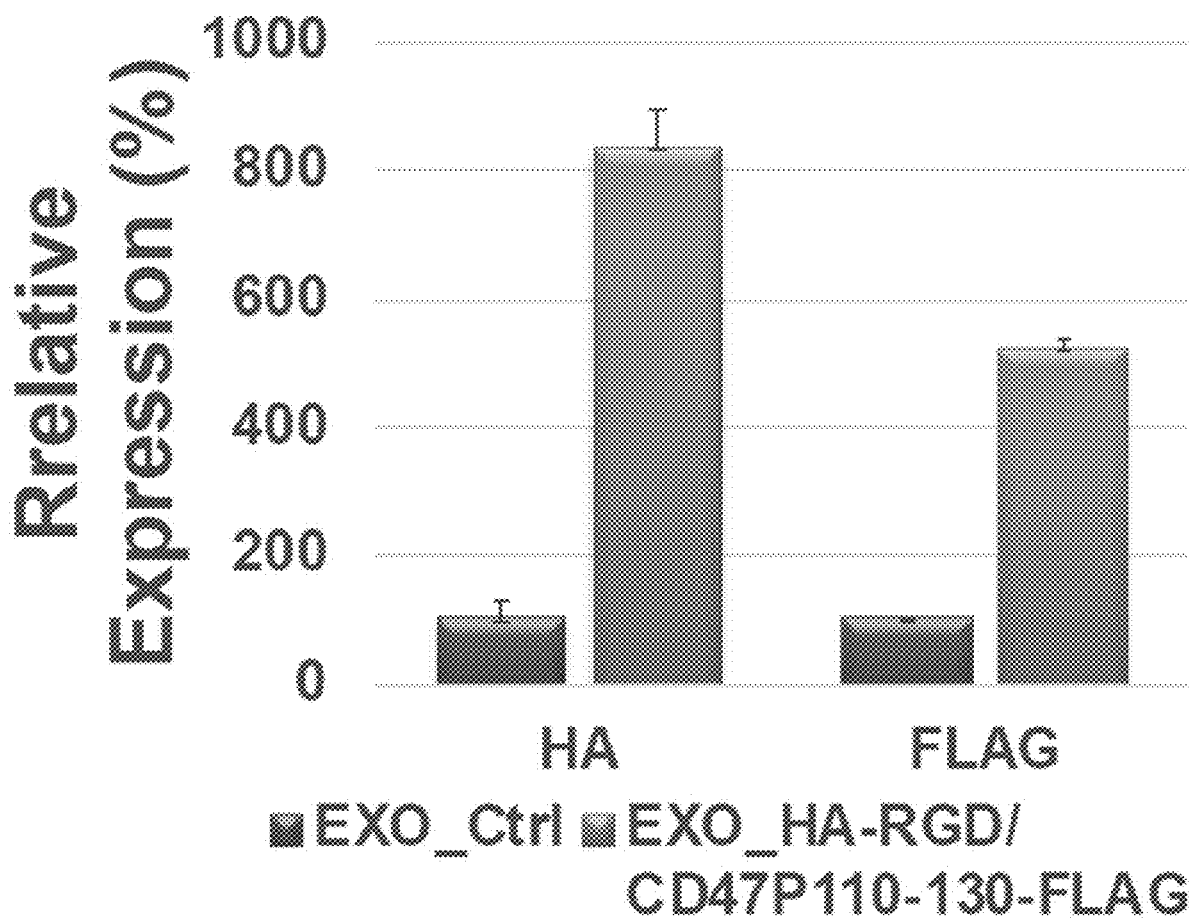
FIGS. 5A-5B: ELISA assay demonstrated displaying both HA-RGD and CD47$^{p110-130-Flag}$ on exosomes (Exo$^{Smart}$) that derived from CD9-HA-RGD and CD9-CD47$^{p110-130-Flag}$ co-transfected HEK 293 cells (FIG. 5A). Exo$^{Smart}$ showed the same binding affinity to αvβ3 and SIRPα as Exo$^{CD9-RGD}$ and Exo$^{CD9-CD47p110-130}$ did, respectively, in an ELISA assay (FIG. 5B).
Figure 5B:
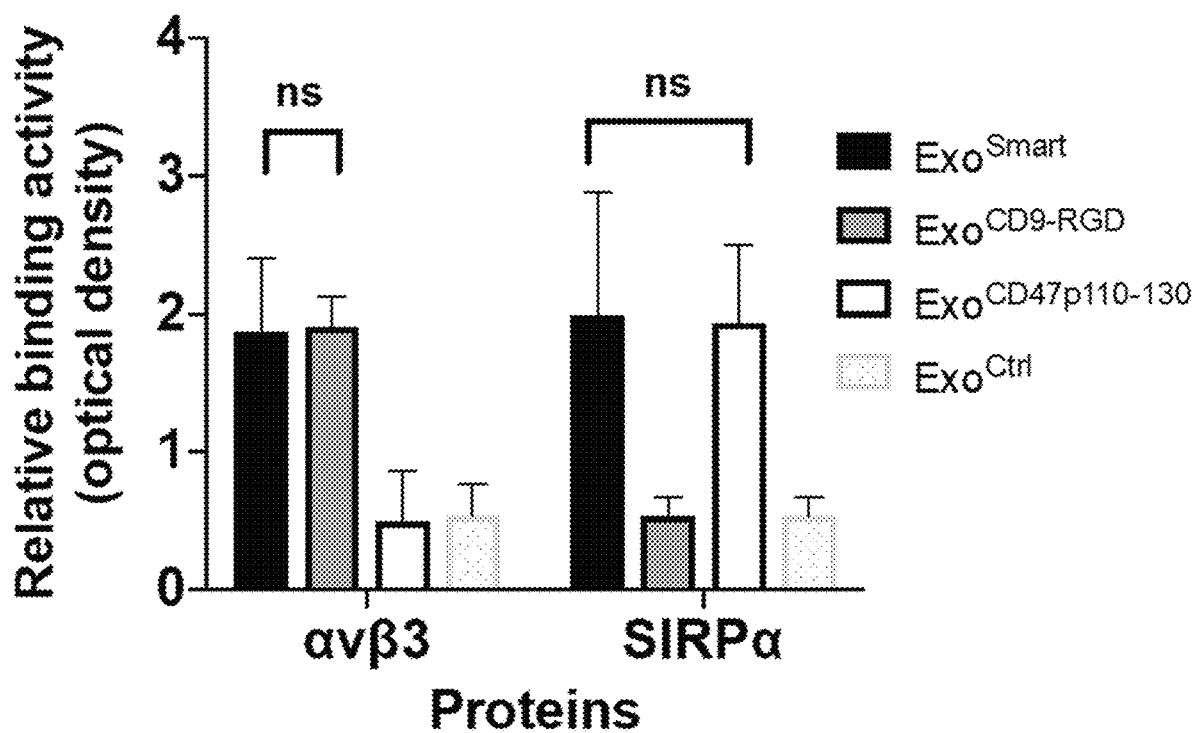

Smart Exosomes Co-Expressing CD9-RGD and CD9-CD47$^{p110\text{-}130}$ Enable Exclusive Active PDAC Tumor Targeting The data in these examples demonstrates successful display of CD9-HA-RGD and CD9-CD47$^{p110\text{-}130\text{-}Flag}$ on exosomes, as tested by ELISA assay (FIG. 5A). Exosomes derived from CD9-HA-RGD and CD9-CD47$^{p110\text{-}130\text{-}Flag}$ co-transfected HEK 293 cells were tested using anti-HA and anti-Flag antibodies, respectively (FIG. 5A). In an ELISA assay, Exo$^{Smart}$ revealed the same binding affinities to αvβ3 and SIRPα as Exo$^{CD9\text{-}RGD}$ and Exo$^{CD9\text{-}CD47p110\text{-}130}$, respectively (FIG. 5B)(experiments in triplicate). This demonstrates that functional CD9-HA-RGD and CD9-CD47$^{p110\text{-}130\text{-}Flag}$ are displayed on exosomes.

CD47p110-130 Peptide Mediated Inhibition of Macrophage Phagocytosis

Figure 6A:
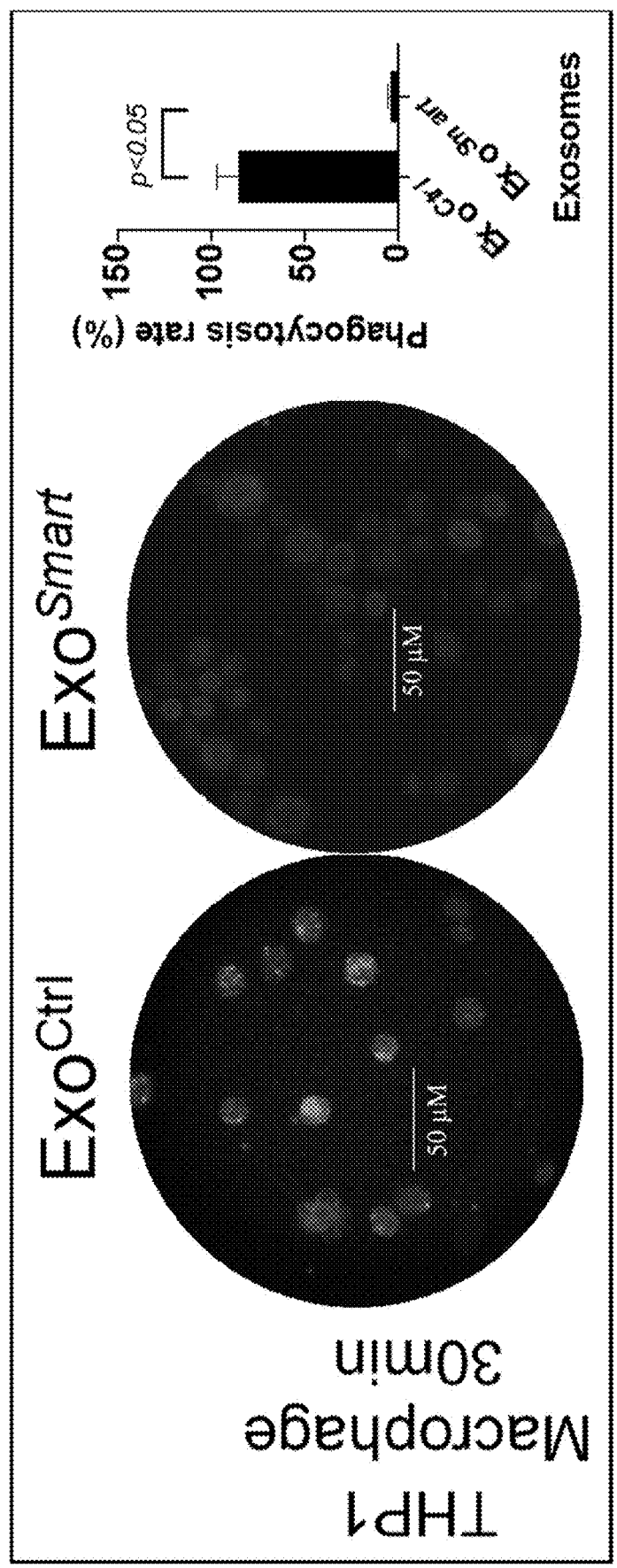
FIGS. 6A-6B: Phagocytosis assay showed that phagocytosis in both induced (FIG. 6A) and uninduced (FIG. 6B) THP-1 cells were significantly inhibited by exosome displaying RGD/CD47$^{p110-130}$ (Exo$^{Smart}$).
Figure 6B:
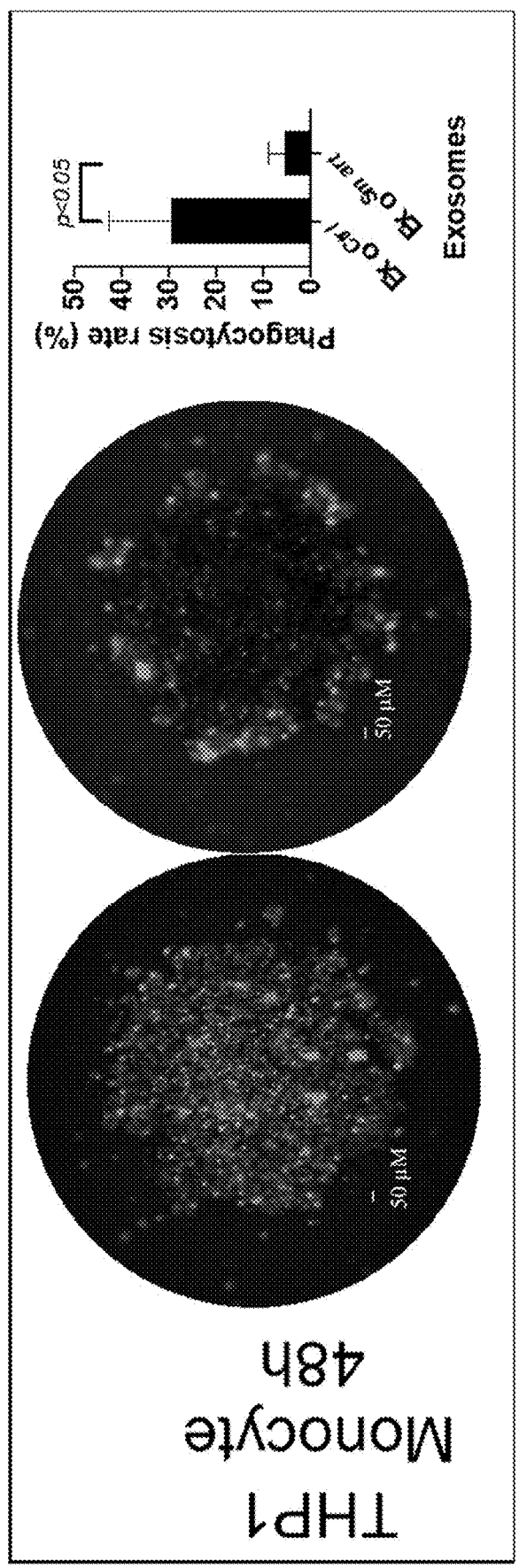

Exo$^{CD9\text{-}RGD/CD47p110\text{-}130}$ (Exo$^{Smart}$) derived from HEK 293 cells was incubated with PMA-stimulated THP1 cells (100 ng/ml, 2 days) for 30 min followed by staining with Hoechst 33342 at 10 ug/ml. Exo$^{Ctrl}$ served as control. Exo man significantly inhibited phagocytosis as compared to Exo$^{Ctrl}$ (p<0.05) (FIG. 6A). The same results were obtained from 48 h incubation of THP-1 cells and exosomes (FIG. 6B, p<0.05). These results demonstrate that CD47$^{p110\text{-}130}$ peptide has the ability to mediate reduction of macrophage phagocytosis.

Exo$^{Smart}$ a Drug Delivery Enhances Cytotoxicity to PDAC Cells

Figure 7:
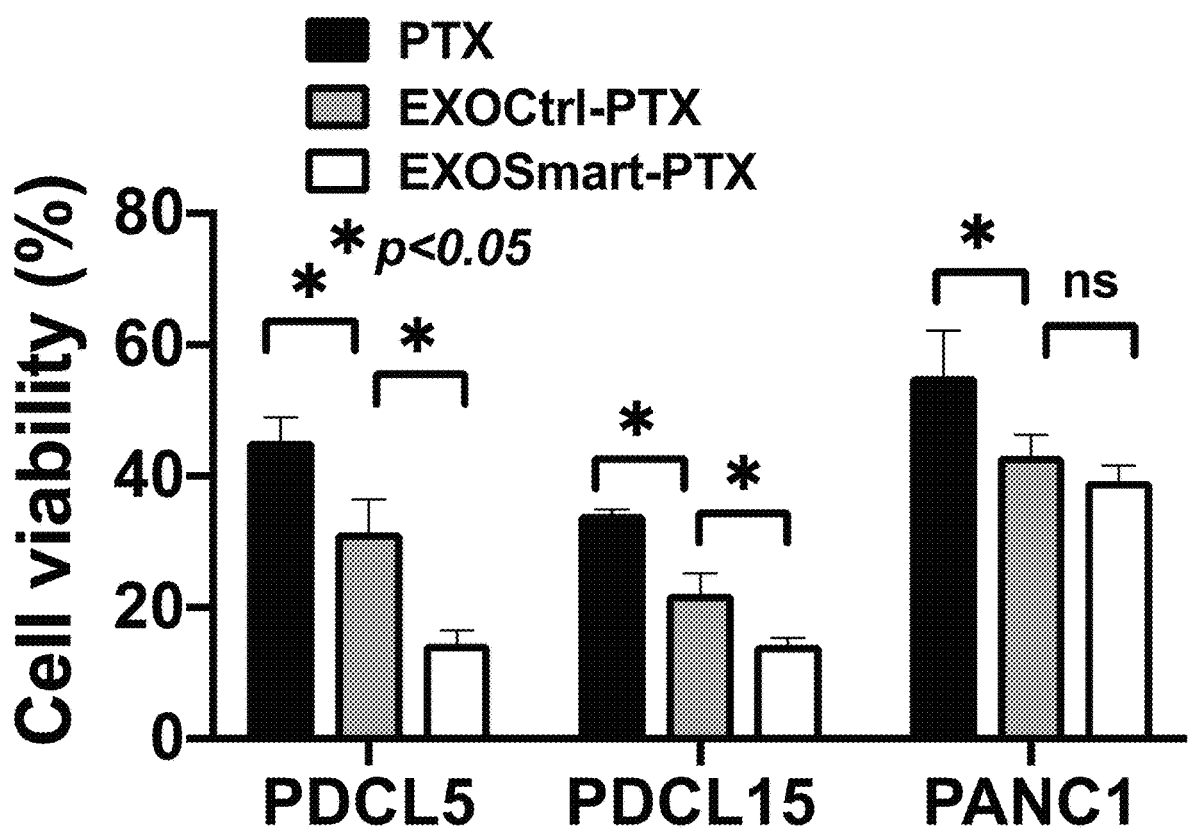
FIG. 7: Cytotoxic effect of Exo$^{Smart}$-PTX on PDAC cells in vitro. Exo$^{Smart}$-FTX resulted in significantly higher cytotoxicity to PDCL5 (high αvβ3 levels) (p<0.05), but not PANC1 cells (low αvβ3 levels) than Exo$^{Ctrl}$-FTX. Both Exo$^{Smart}$-PTX and Exo$^{Ctrl}$-PTX were superior to PTX in terms of cytotoxicity to PDAC cells (p<0.05).

Exo$^{Smart}$-PTX and Exo$^{Ctrl}$-PTX were generated by directly mixing 15 μg Exo$^{Smart}$ or Exo$^{Ctrl}$ with 10 μM of paclitaxel (PTX) in 100 μl PBS. Purified Exo$^{Smart}$-PTX, Exo$^{Ctrl}$-PTX, and PTX were applied on PDCL5 (high αvβ3 levels) and PANC1 cells (low αvβ3 levels) at final PTX concentration of 100 nM. Cell viability was determined by CellTiter Glo assay (experiments in triplicate). The data showed significantly enhanced cytotoxic effect of Exo$^{Smart}$-PTX and Exo$^{Ctrl}$-PTX on both PDCL5 and PANC1 as compared to PTX. Exo$^{Smart}$-FTX had a greater effect on PDCL5 than Exo$^{Ctrl}$-FTX (p<0.05) (FIG. 7), which was consistent with the expression of αvβ3 on these cells. These data demonstrate that exosome-based delivery systems increase drug effects, and the smart exosomes can effectively deliver drugs such as paclitaxel to pancreatic cancer cells.

Materials and Methods

Construction of Plasmid

N terminal mCherry tagged CD9 vectors (mCherry-CD9) were received as a gift (Addgene plasmid #55013). HA tagged RGD-4C (HA-RGD) oligos (TACCCATAC-GATGTTCCAGATTACGCTTGCGATTGCCGTGGC-GATTGCTGC (SEQ ID NO: 3)) and Flag tagged (CD47$^{p110\text{-}130}$-FLAG) GGAAACTACACTTGT-GAAGTAACAGAATTAACCAGAGAAGGTGAAAC-GATCATCGAGCTAAA AGATTACAAGGATGACGAC-GATAAG (SEQ ID NO: 4)) oligos was synthesized in Integrated DNA Technologies, Inc. (Coralville, Iowa). The oligos were inserted into CD9 vector at E174 and T175 using Q5® Site-Directed Mutagenesis Kit (New England Biolabs Inc, Ipswich, MA) following the manufacturer's instructions. Finally, the pcDNA-mCherry-CD9$^{HA\text{-}RGD}$ and CD9$^{CD47p110\text{-}13\text{-}FLAG}$ vectors were constructed. The resultant peptide sequences were HA-RGD: YPYDVPDY-ACDCRGDCFC (SEQ ID NO: 5), and CD47$^{p110\text{-}130}$-FLAG: GNYTCEVTELTREGETIIELKDYKDDDDK (SEQ ID NO: 6).

Transfection

The HEK 293T cells were seeded in 25-cm$^2$ flasks (NUC; Thermo Fisher Scientific, Waltham, MA, USA). Cells at 70%-80% confluence were transfected with the CD9$^{HA\text{-}RGD}$ or CD9$^{CD47p110\text{-}13\text{-}FLAG}$ plasmid using Lipofectamine 3000 (Invitrogen) as described by the manufacturer. The 293T cells were analyzed for mCherry expression 48 h after the transfection (red fluorescence protein).

Exosomes Collection

Ultracentrifugation

Cell culture media (CCM) was harvested from HEK 293 cells and centrifuged using a Thermo Sorvall Legend XTR centrifuge at 3000 g at 4° C. for 15 minutes to remove detached cells. Supernatant was collected and filtered through 0.22 μm filters (MilliporeSigma) to remove contaminating apoptotic bodies, microvesicles, and cell debris. Clarified CCM was then centrifuged in a Beckman L8-60M Ultracentrifuge at 100,000 g avg at 4° C. for 90 minutes with a Type 70.2 Ti rotor (k-factor: 157.7) to pellet exosomes. The supernatant was carefully removed, and crude exosome-containing pellets were resuspended in 1 mL of ice-cold PBS and pooled.

ExoQuick™ Precipitation

Exosome isolation from CCM ExoQuick™ precipitation was carried out according to the manufacturer's instructions (System Biosciences). Briefly, 500 μL of clarified CCM was diluted to 5 mL in PBS and mixed with 1 mL of ExoQuick-TC™ solution by inverting the tube several times. The sample was incubated overnight at 4° C. then centrifuged twice at 1,500 g for 30 and 5 minutes, respectively, in order to remove the supernatant. The supernatant was discarded, and the pellet was resuspended in 200 μL of PBS.

Exosome Purification

Size Exclusion Purification

Five-hundred microliters of clarified CCM was overlaid on qEV size exclusion columns (Izon) followed by elution with PBS. Five-hundred-microliter fractions were collected, and particle and protein concentrations were determined with Nanodrop (ThermoFisher). High particle/low protein fractions from CCM were pooled and concentrated in Amicon® Ultra-4 10 kDa nominal molecular weight centrifugal filter units to a final volume of 100 µL.

Example II

Figure 8A:
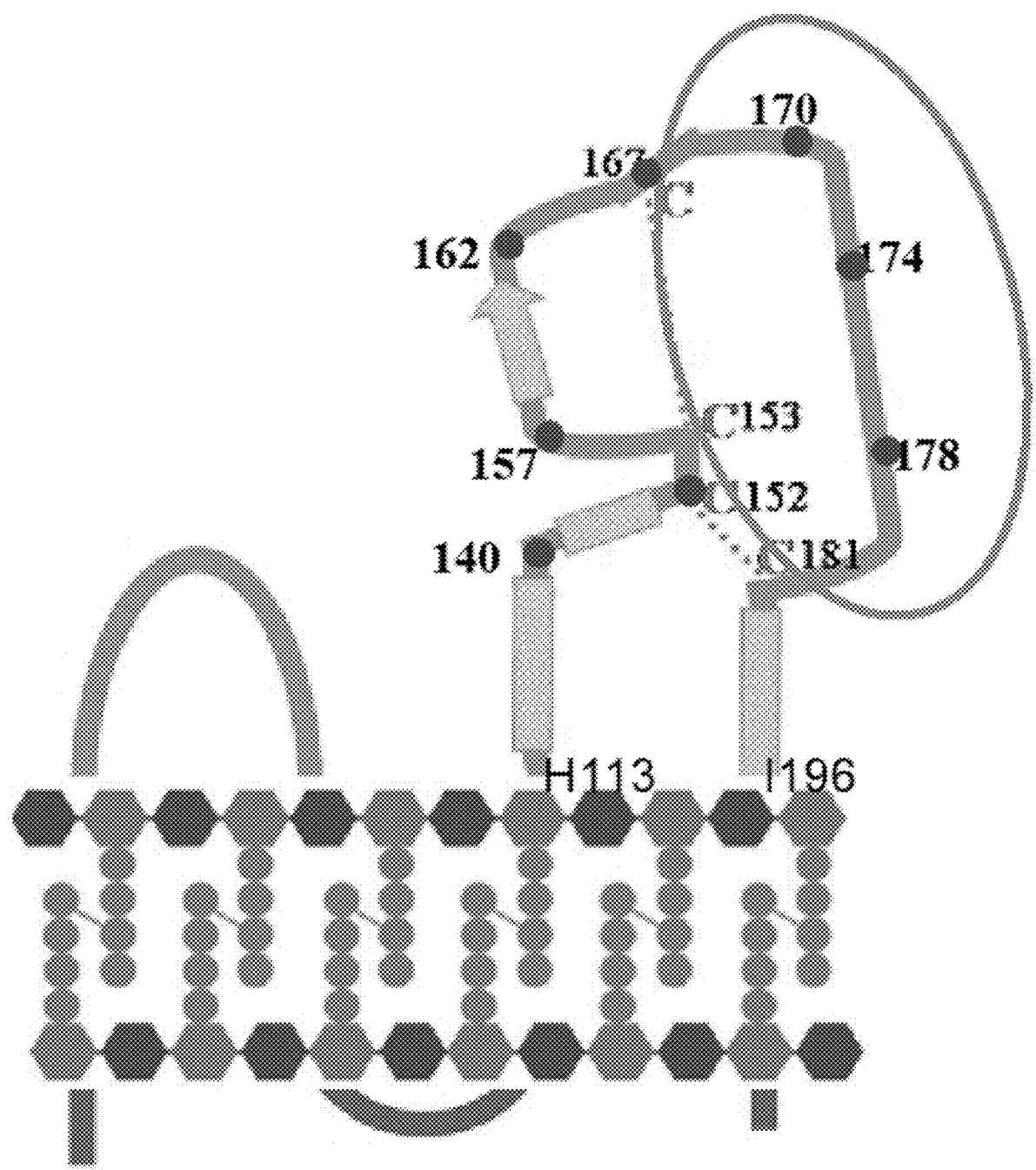
FIGS. 8A-8D: CD9 multiple engineering sites determined by incorporation of HA into different sites of LEL (FIG. 8A). Western blot demonstrates strong expression of HA at C167, K170, E174, and V178 in cell lysate and exosomes. Insertion of HA and FLAG at E174 and V178 of CD9 results in co-expression of HA and FLAG on exosome (FIG. 8D).
Figure 8B:
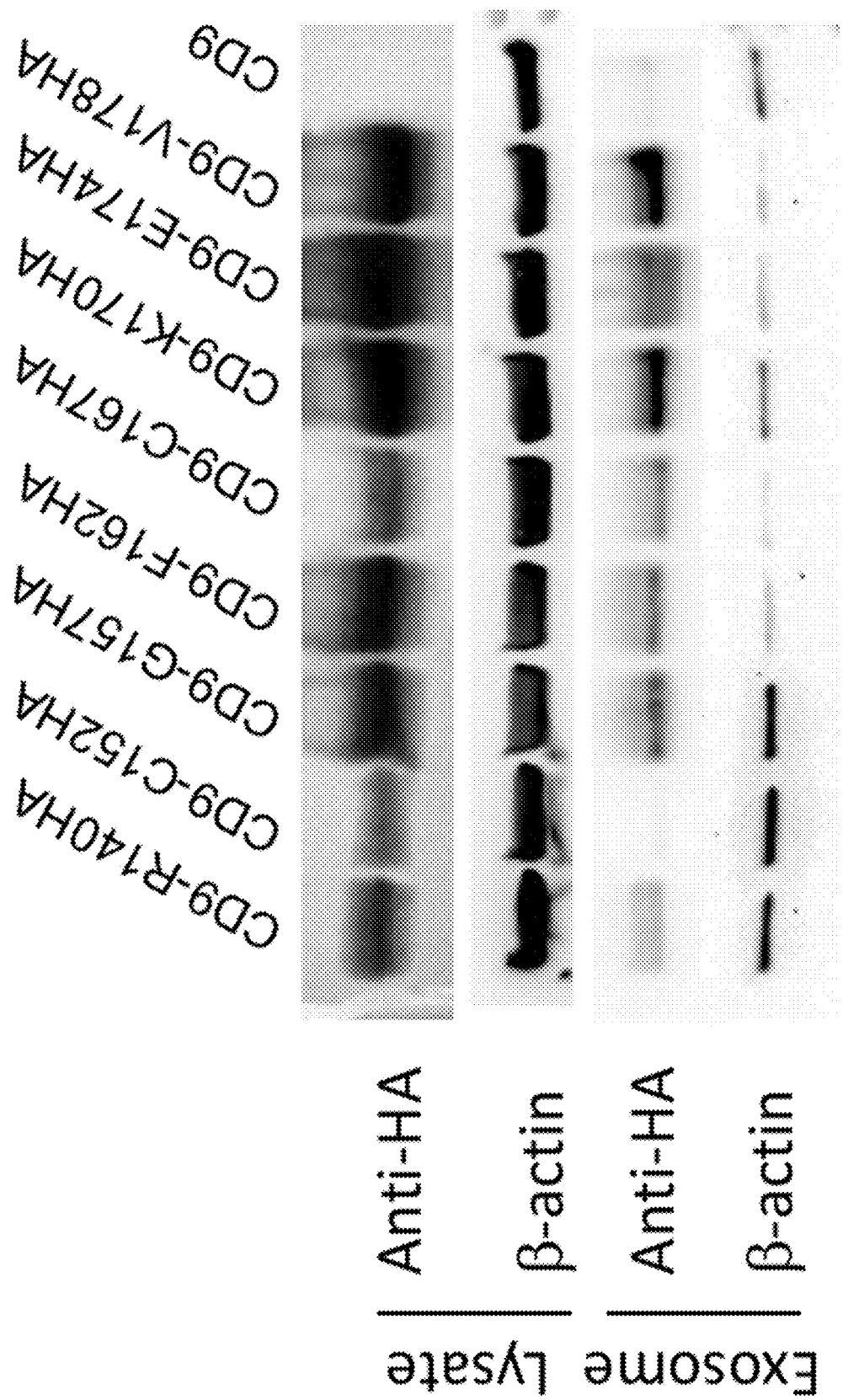
Figure 8C:
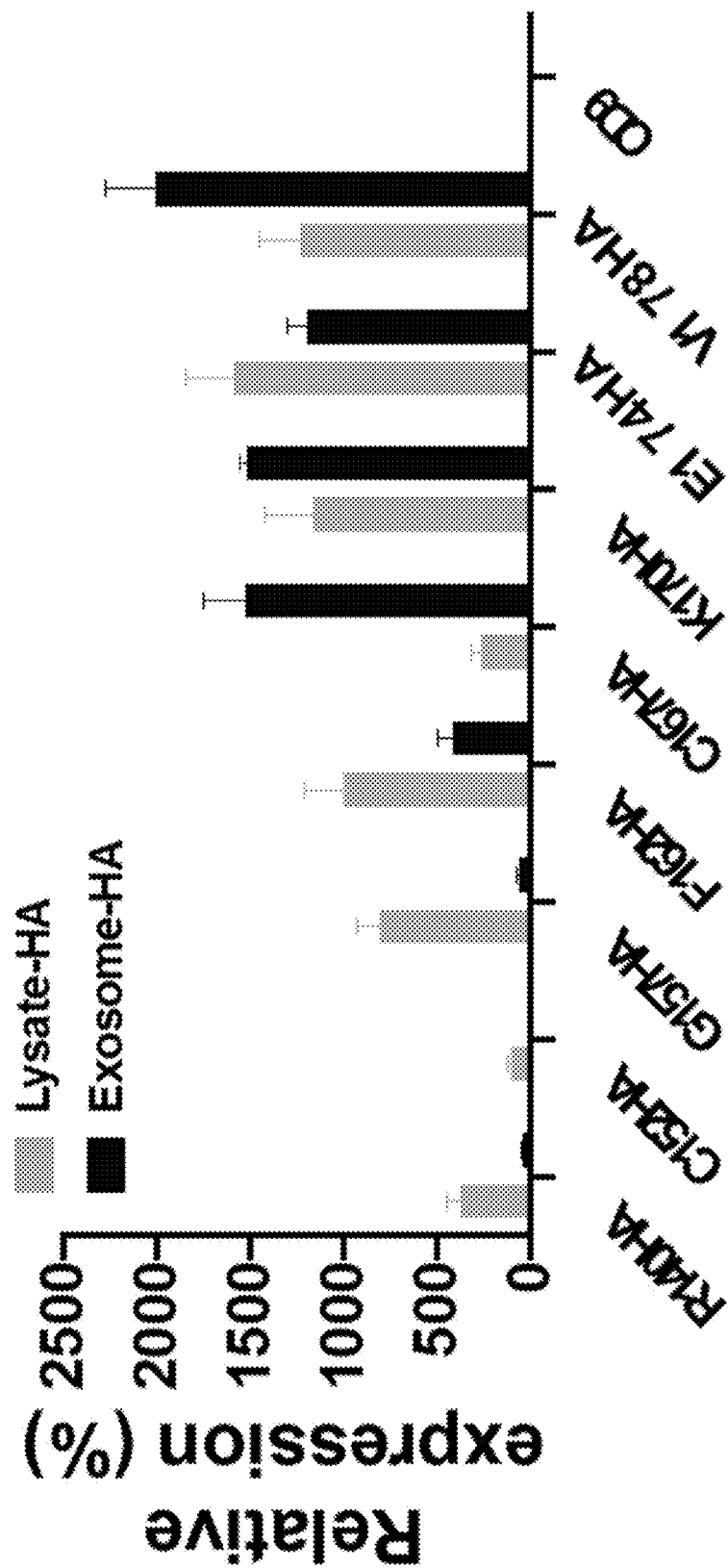
Figure 8D:
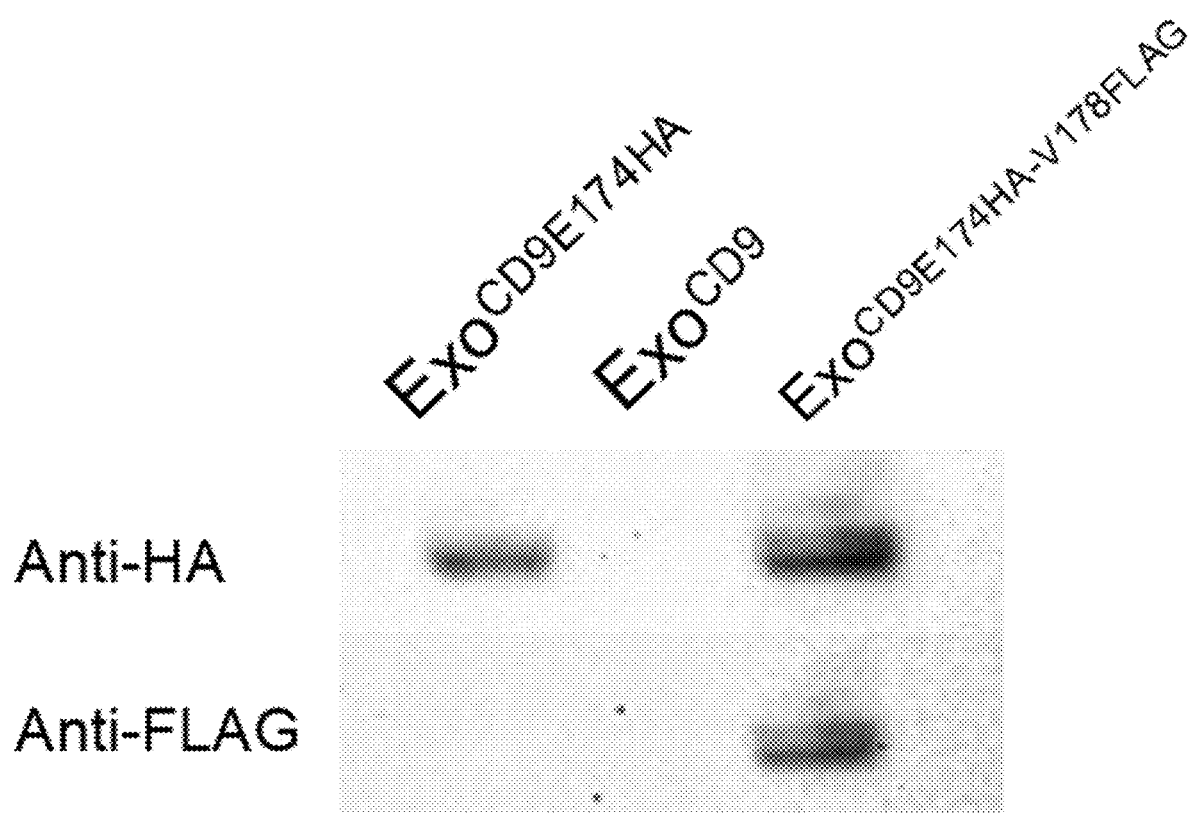

Multiple engineering sites were determined by incorporation of HA into different sites of the CD9 LEL, as depicted in FIG. 8A. Western Fblots demonstrated a strong expression of HA at C167, K170, E174, and V178 in cell lysate and exosomes (FIGS. 8B-8C). HA and FLAG were inserted at E174 and V178 of CD9, resulting in co-expression of HA and FLAG on the exosomes (FIG. 8D).

Figure 9A:
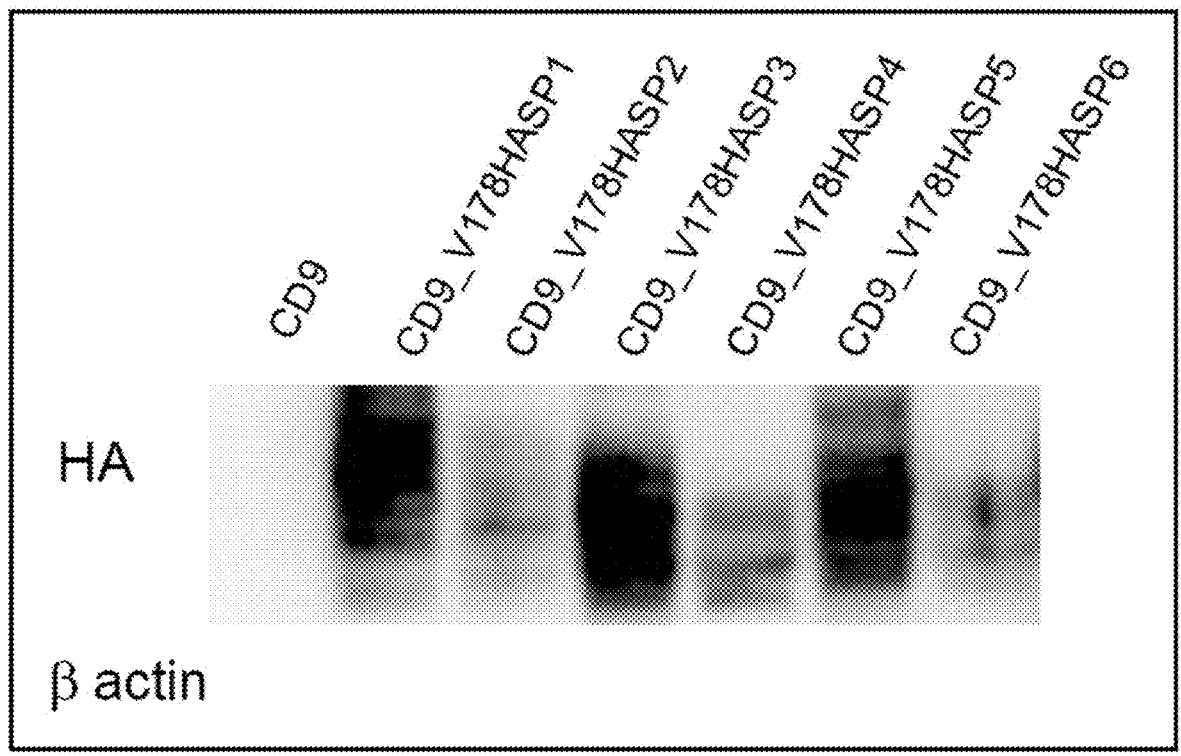
FIGS. 9A-9C: CD47 self-peptides (SPs) screening. Six peptides were designed, HA tagged, and incorporated into CD9 at V178. Overexpression of SPs and SIRPα in HEK293 showed varied expression of SP (FIG. 9A) and varied SPs-SIRPα binding capabilities (FIG. 9B). SP5 was overexpressed in transfected HEK293 cells.
Figure 9B:
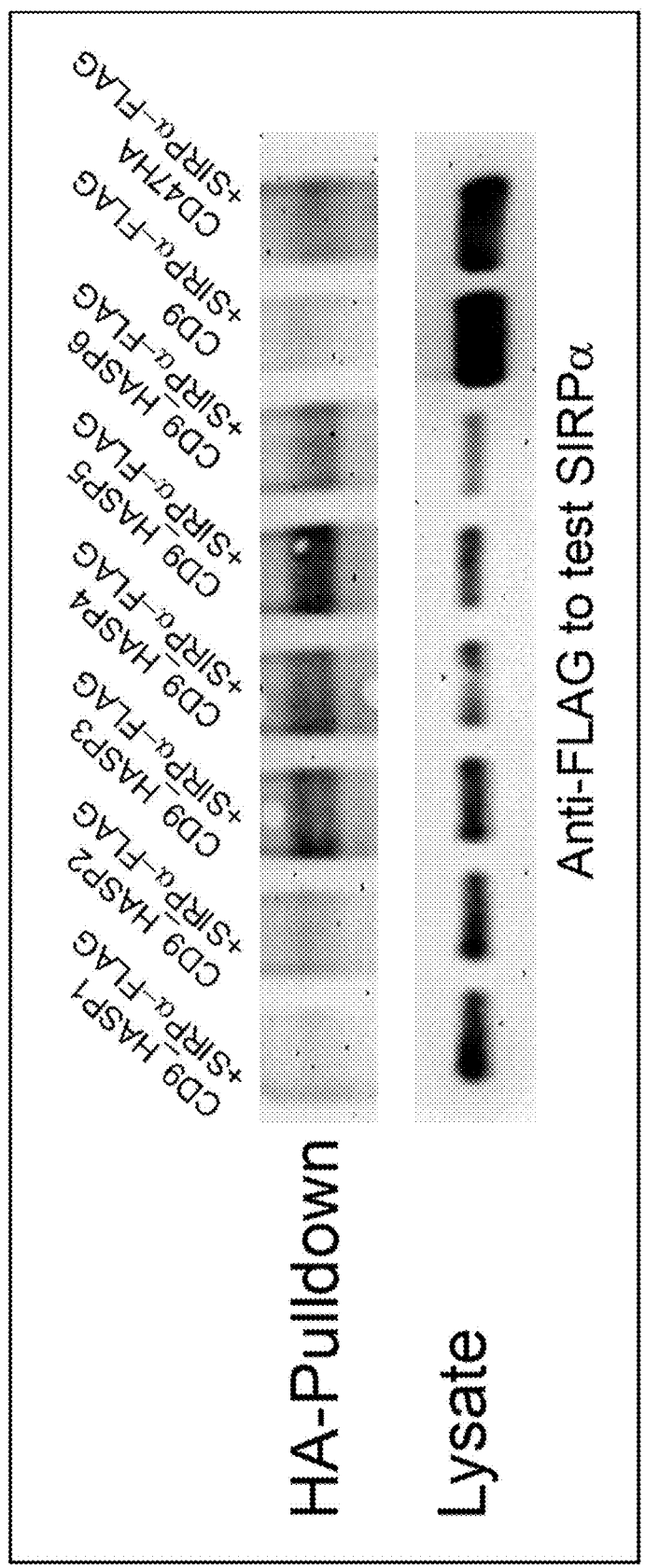
Figure 9C:
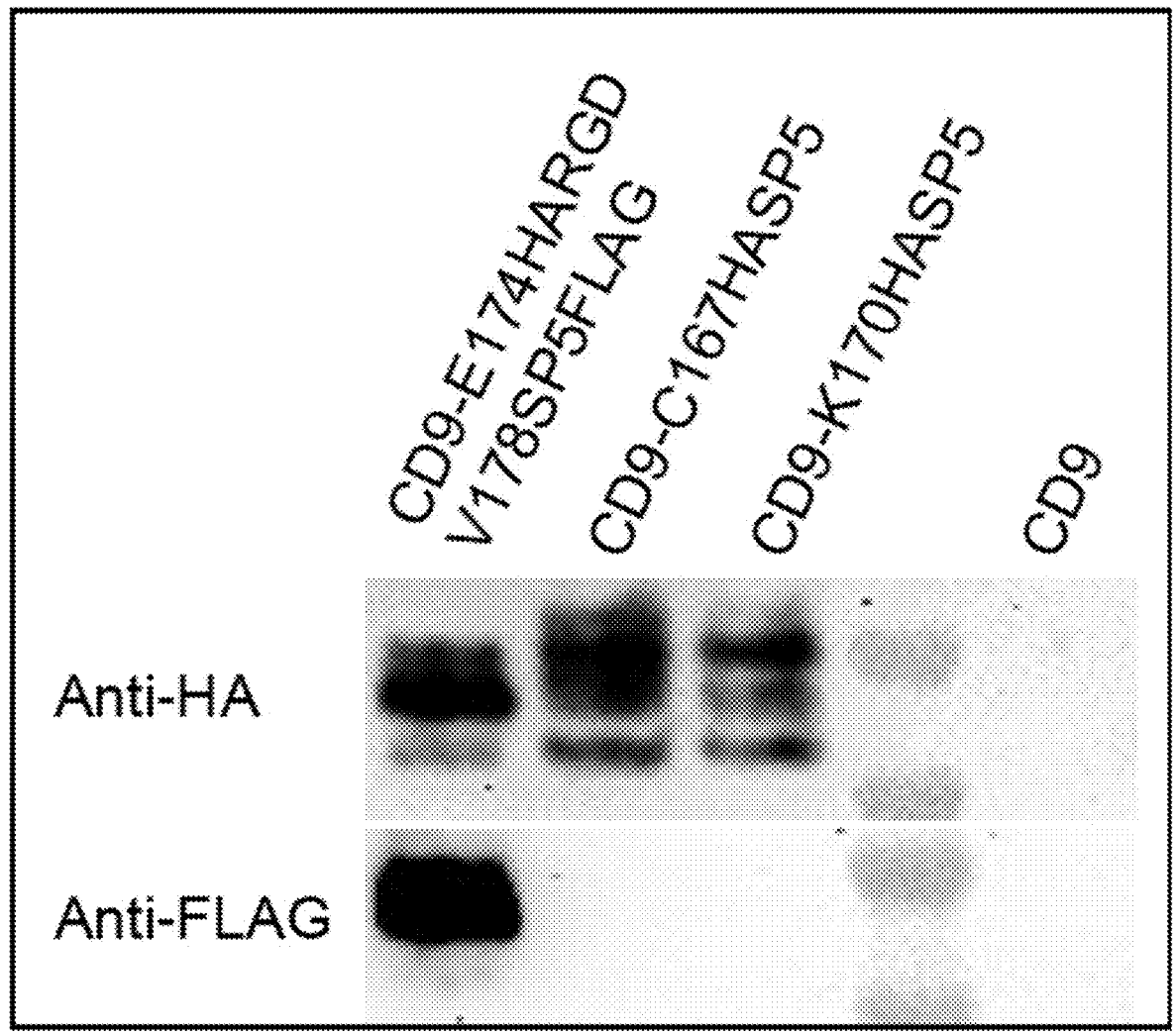

Based on CD47 self-peptides (SPs) screening, six peptides were designed, HA tagged, and incorporated into CD9 at V178. (FIGS. 9A-9C.) Overexpression of the SPs and SIRPα in HEK293 cells showed varied expression of the SPs (FIG. 9A) and varied self-peptides-SIRPα binding capabilities (FIG. 9B). Self-peptide 5 (SP5) was overexpressed in transfected HEK293 cells.

Figure 10A:
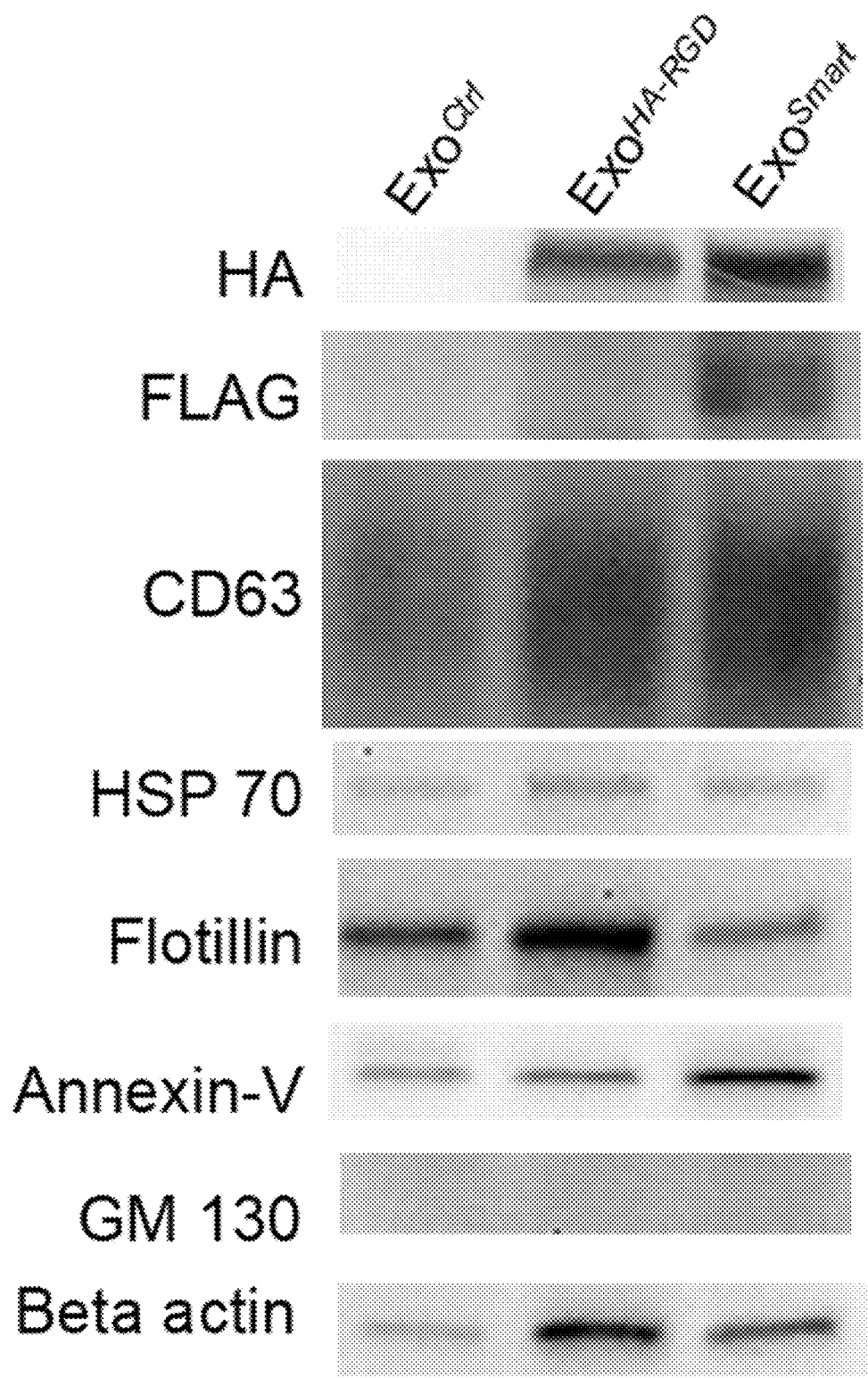
FIGS. 10A-10E: Exo$^{Smart}$ characterization. Exo$^{Smart}$ was featured with exosomal biomarkers as well as HA-RGD and CD47$^{p110-130}$-FLAG expression as determined by western blot (FIG. 10A). The size of Exo$^{Smart}$ is around 100 nm (C:TEM). Exo$^{Smart}$ displaying HA and FLAG peptides were also validated by ELISA (FIG. 10B) and FCM (FIG. 10D, FIG. 10E) assays.
Figure 10B:
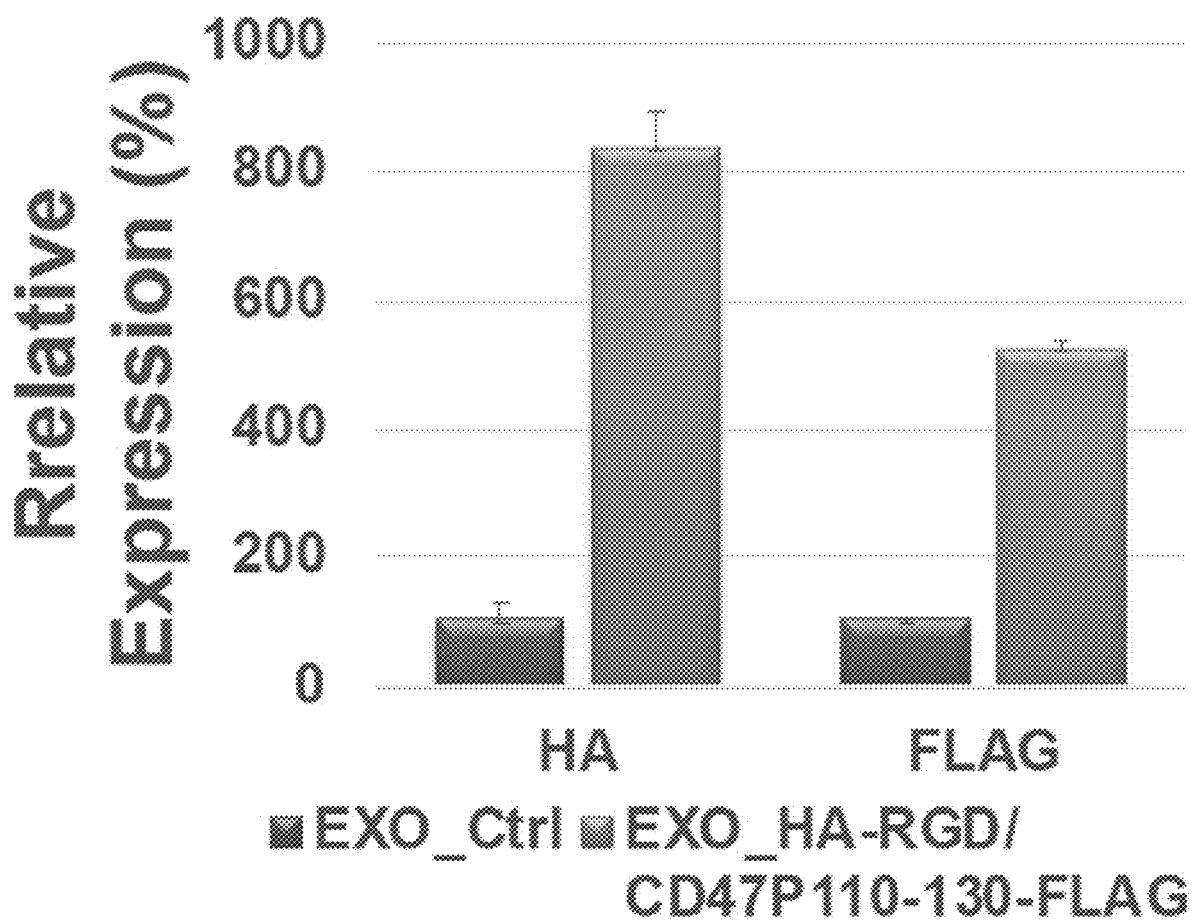
Figure 10C:
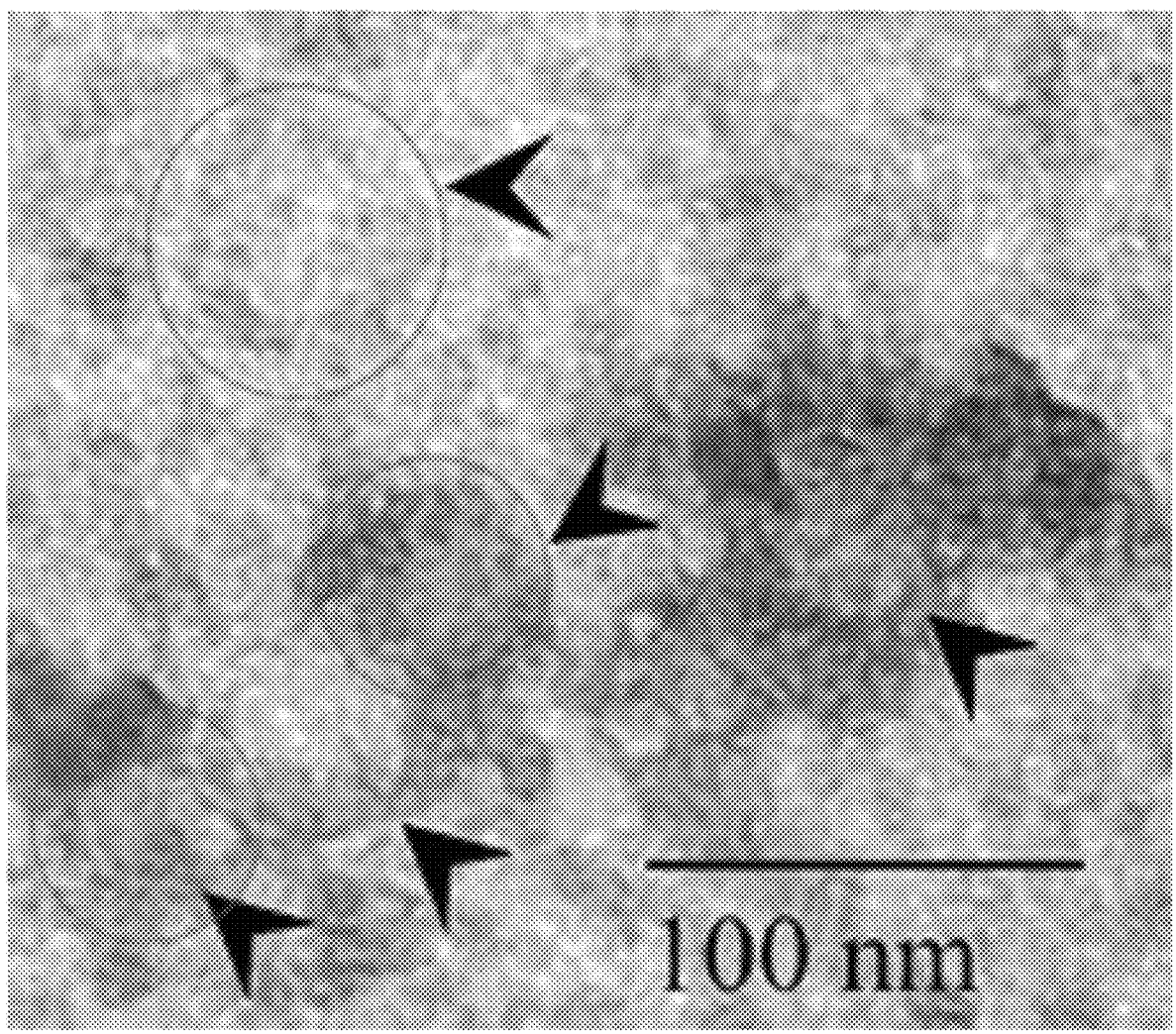
Figure 10D:
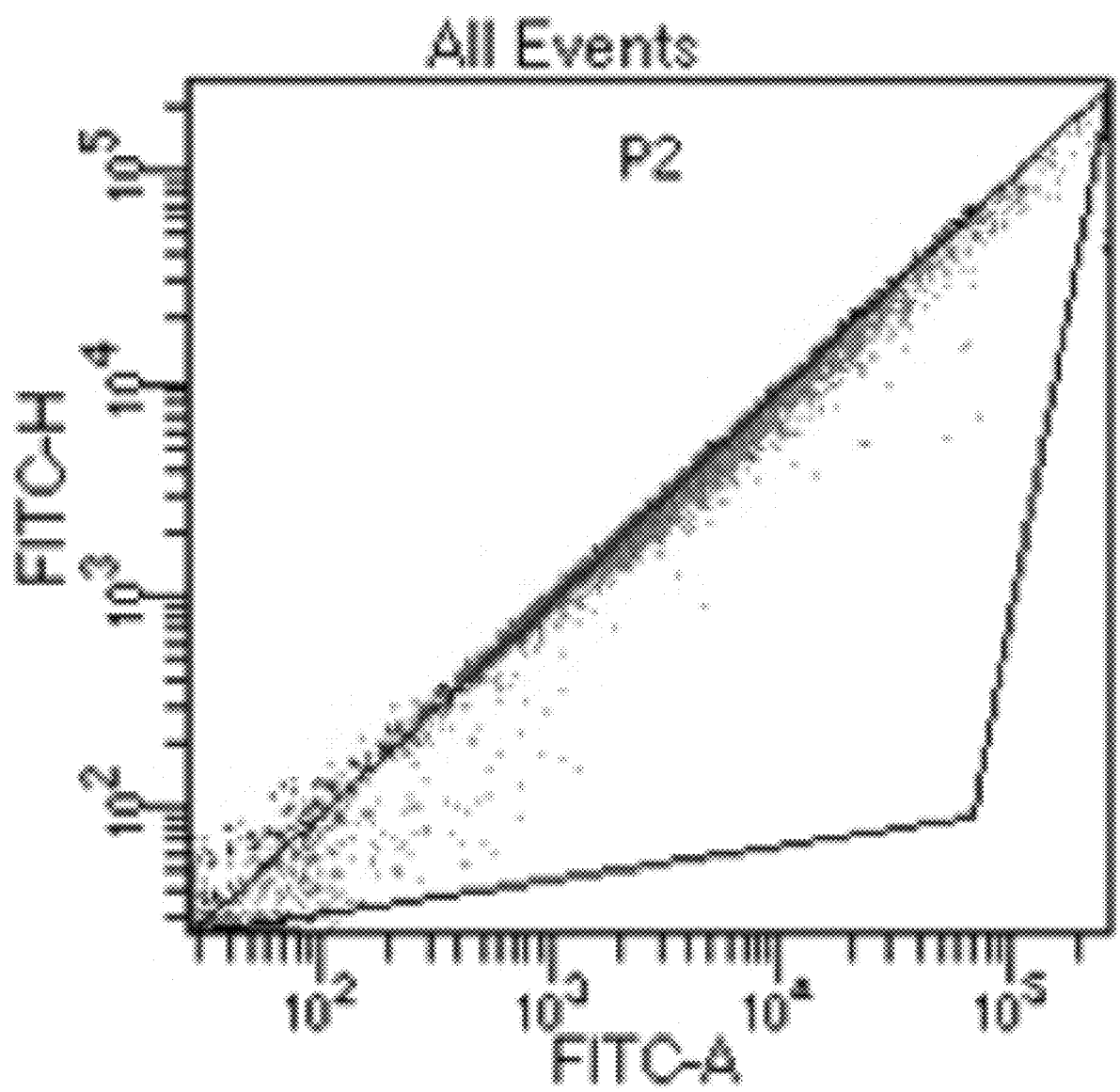
Figure 10E:
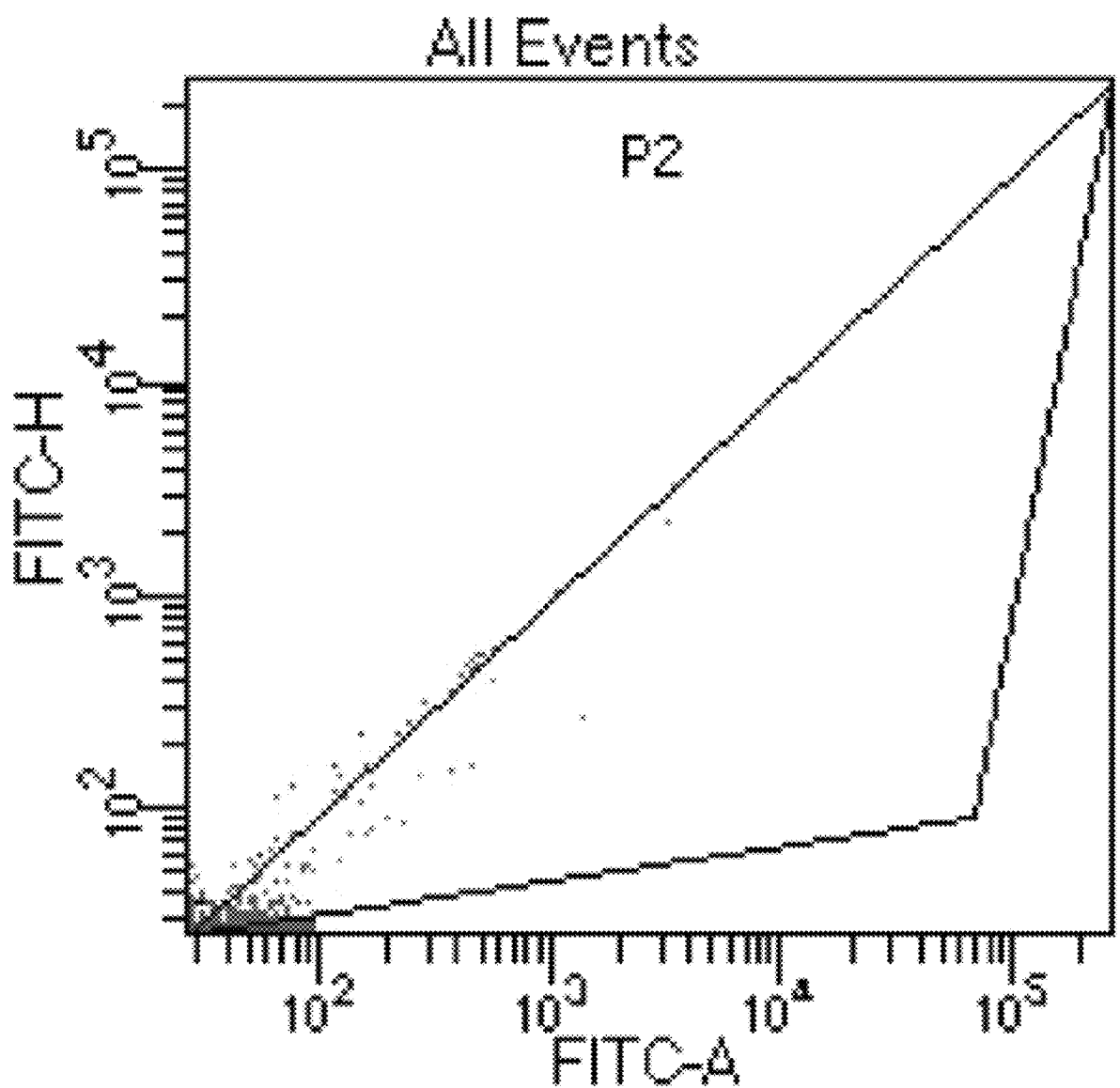
Figure 11A:
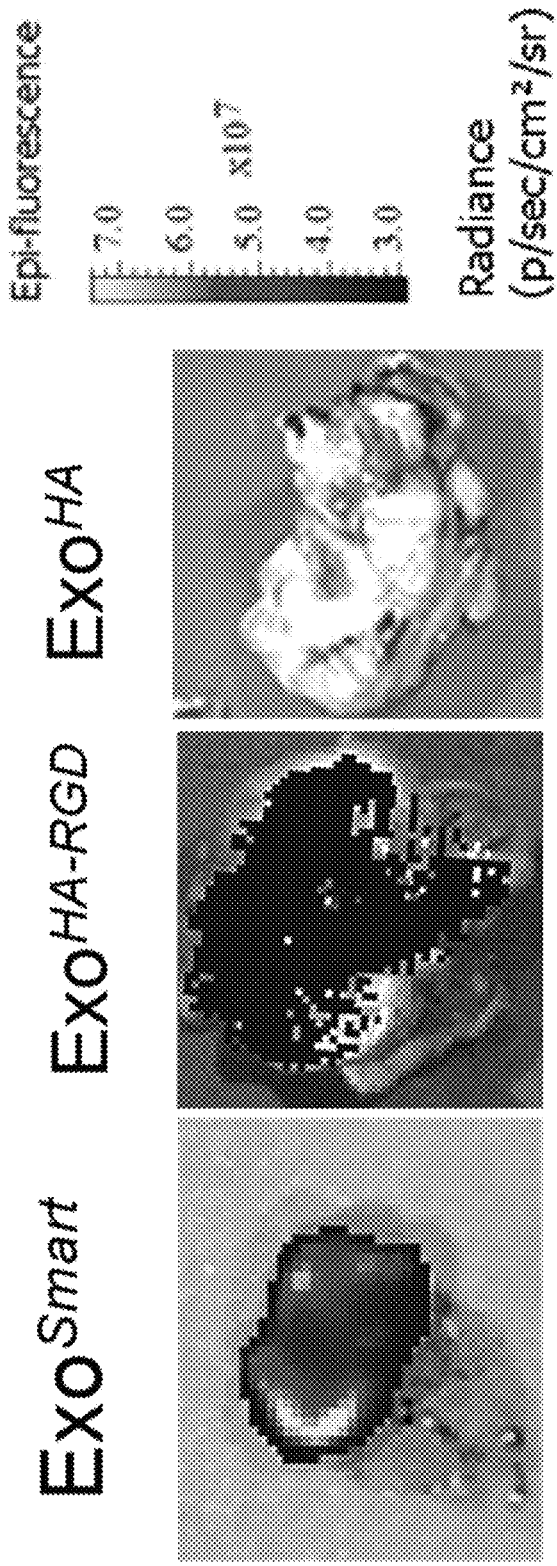
FIGS. 11A-11C: Exo$^{Smart}$ penetrates ECM in TME and targets αvβ3 expressing cells. The tumors from Exo$^{Smart}$, Exo$^{HA-RGD}$ and Exo$^{HA}$ injected PDCL5/PSC mice were stained with anti-fibronectin, anti-αvβ3 (top panel in FIG. 11C), anti-HA (middle panel in FIG. 11C), and HE (bottom panel in FIG. 11C). Exo$^{Smart}$ group showed stronger HA signal (left column) than Exo$^{HA-RGD}$ (middle column) and Exo$^{HA}$ (right column). Strong fibronectin-staining was also shown in Exo$^{Smart}$ group. Scale bar: 50 μm.
Figure 11B:
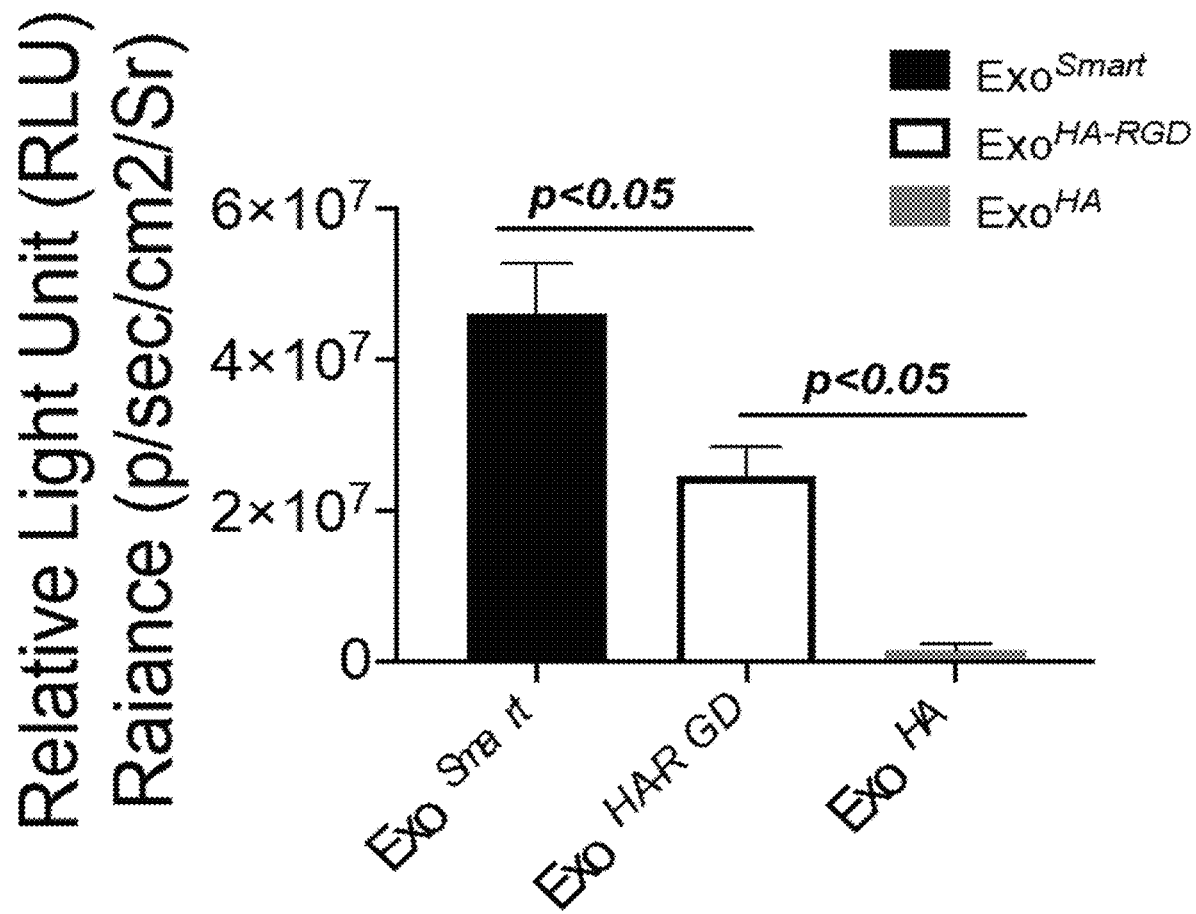
Figure 11C:
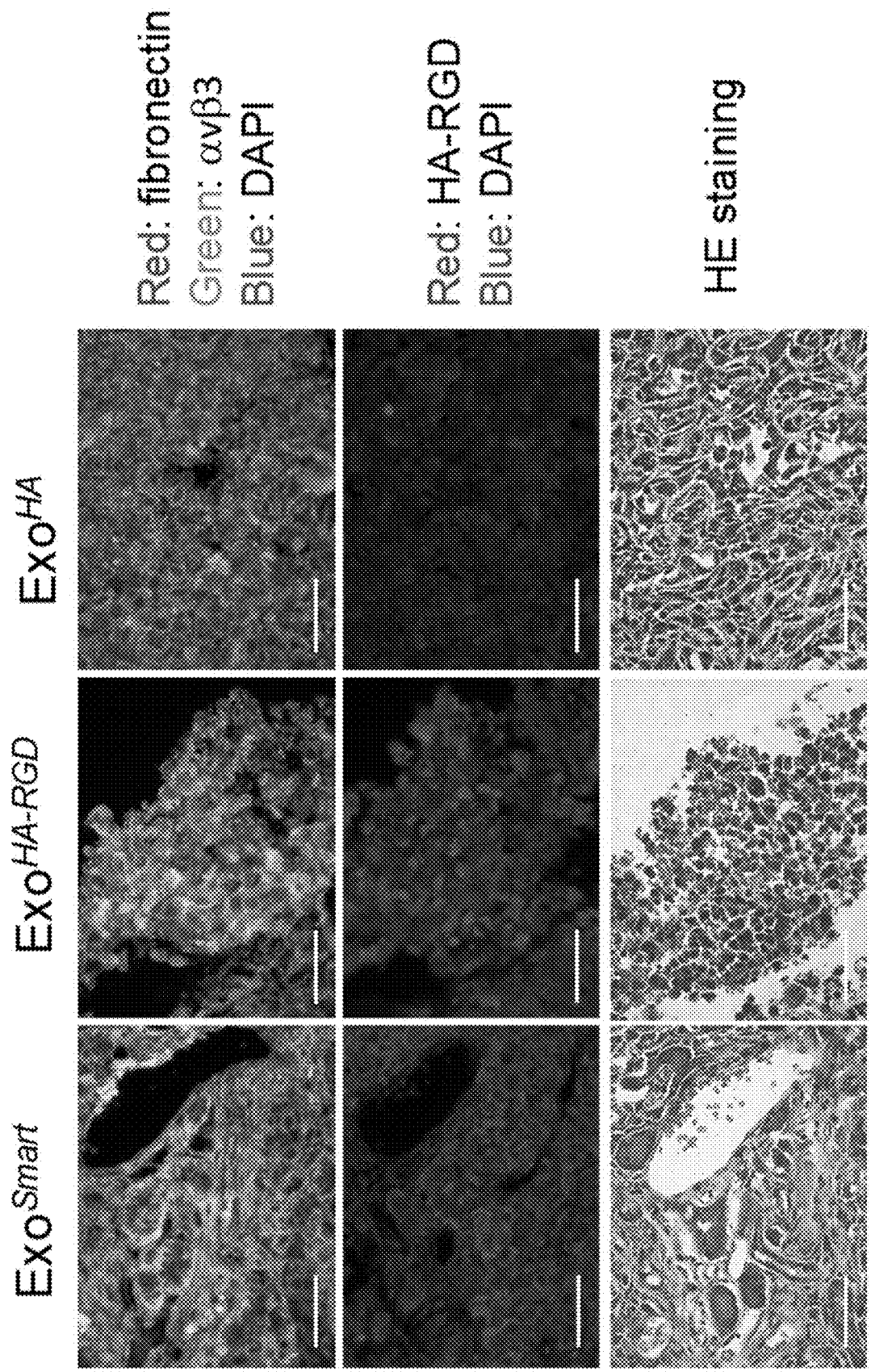
Figure 12A:
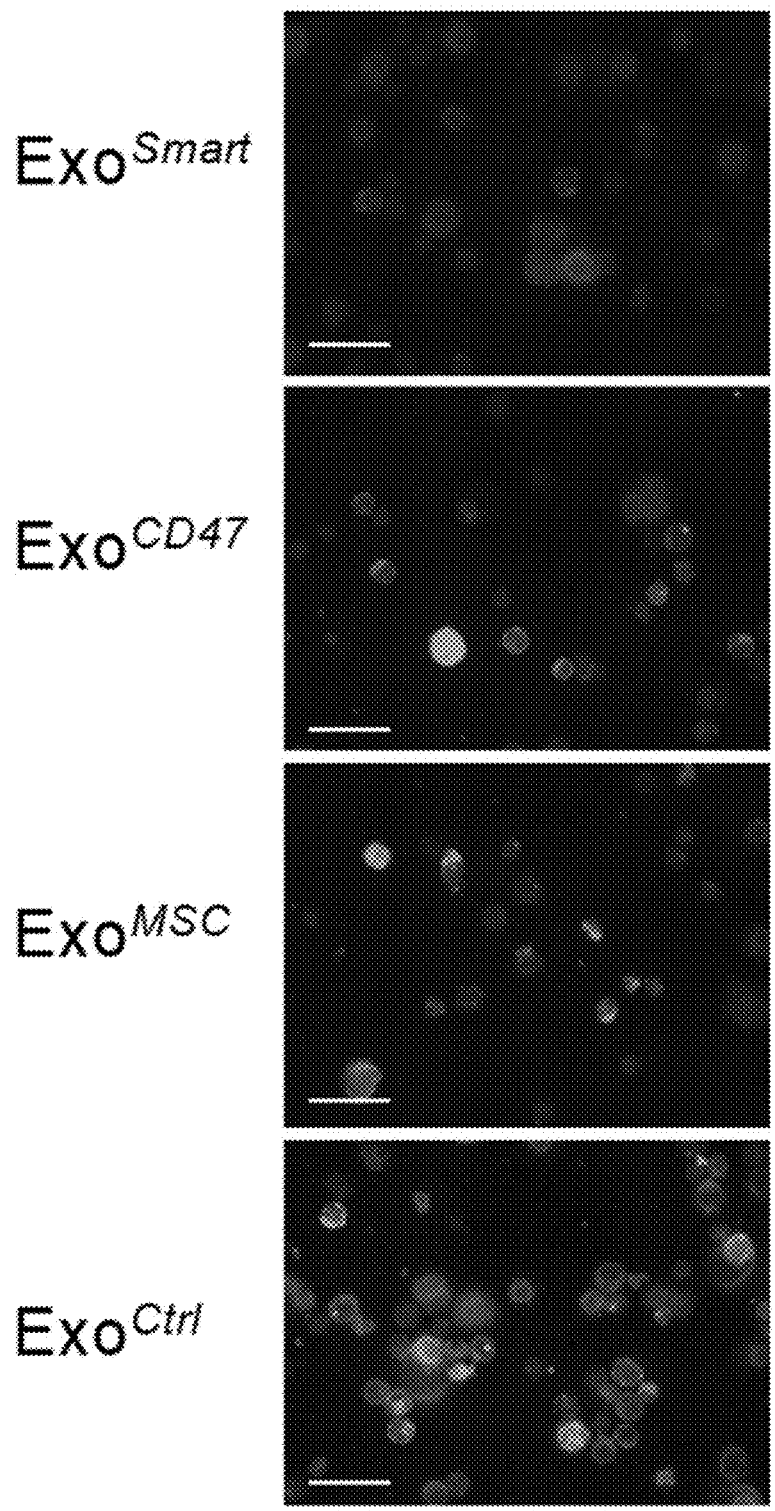
FIGS. 12A-12E: A phagocytosis assay showed that phagocytosis in PMA-induced THP-1 cells was significantly inhibited by exosomes displaying Exo$^{Smart}$ (FIG. 12A). The expression of CD9$^{CD47p110-130}$ on Exo$^{Smart}$ (FIG. 12B, FIG. 12D), CD47 on Exo$^{CD47}$ and Exo$^{MSC}$ (FIG. 12C, FIG. 12E) was determined by western blot detecting FLAG and CD47.
Figure 12B:
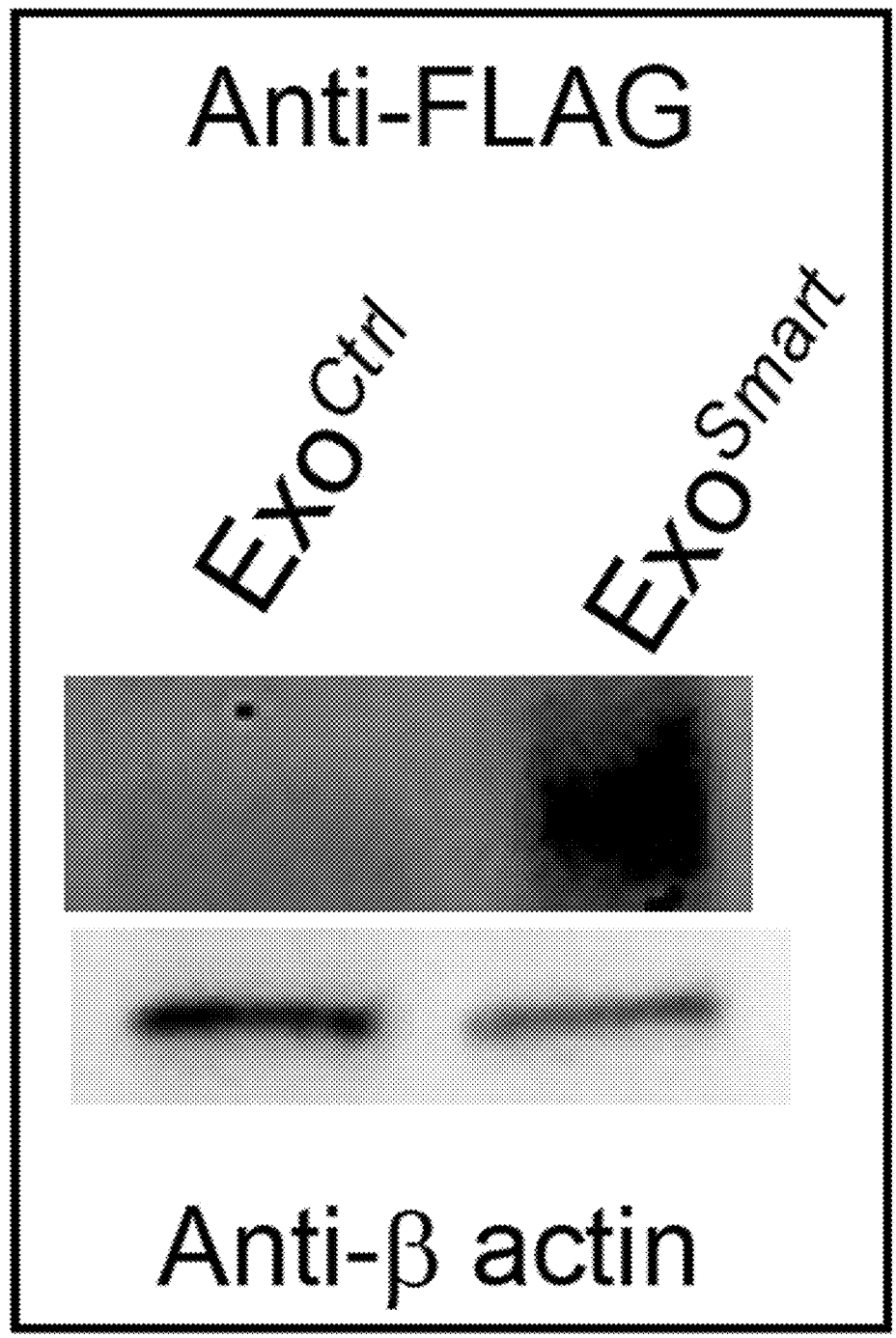
Figure 12C:
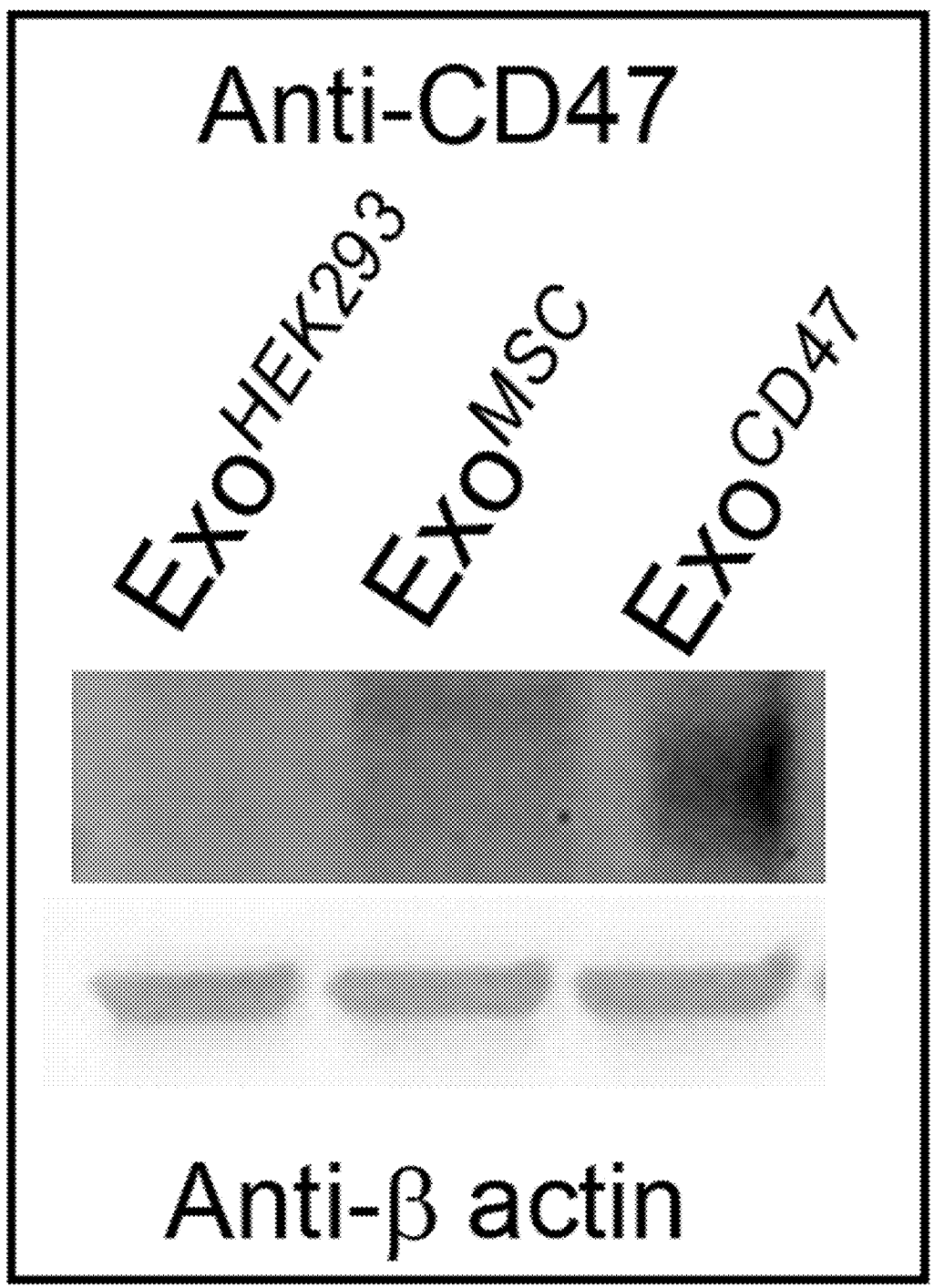
Figure 12D:
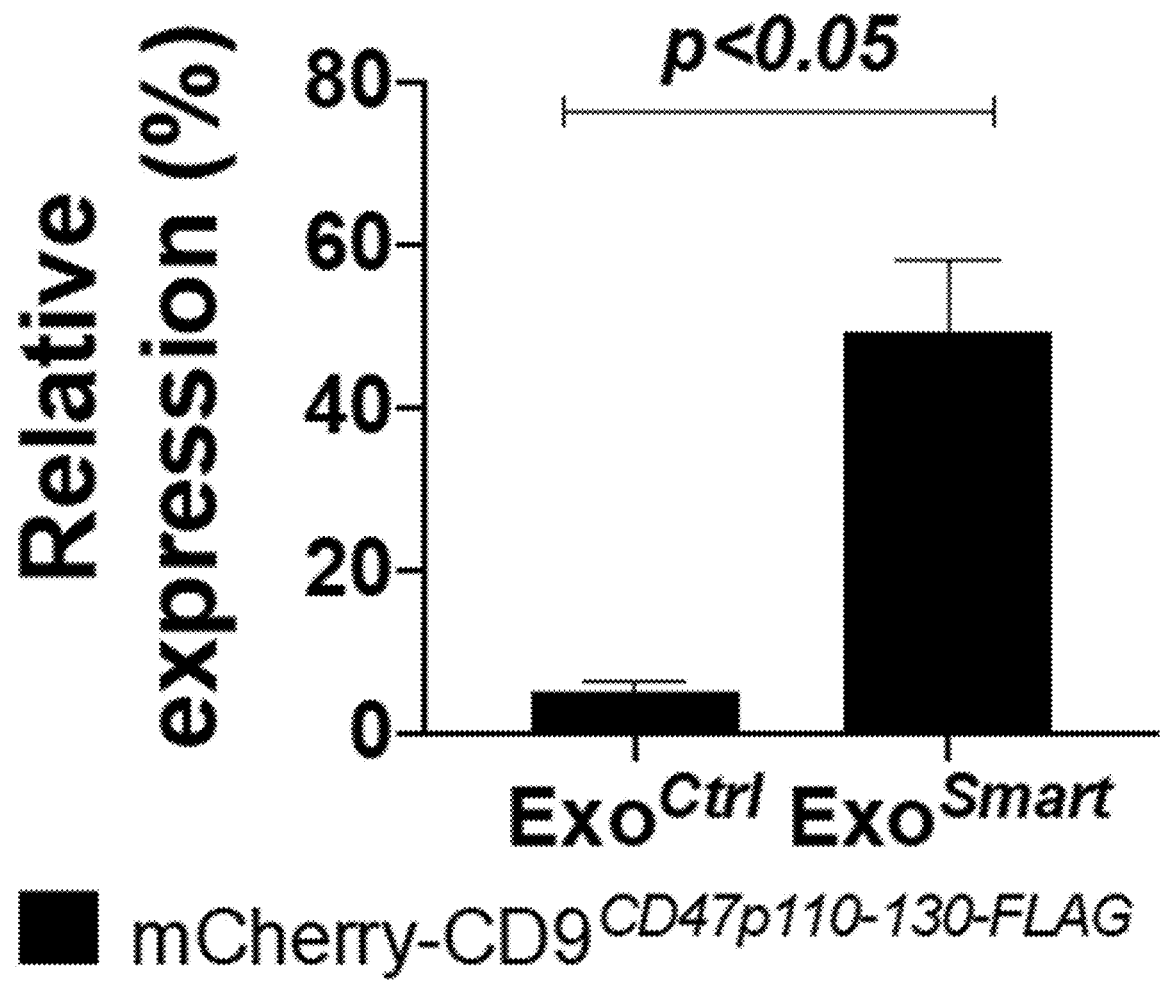
Figure 12E:
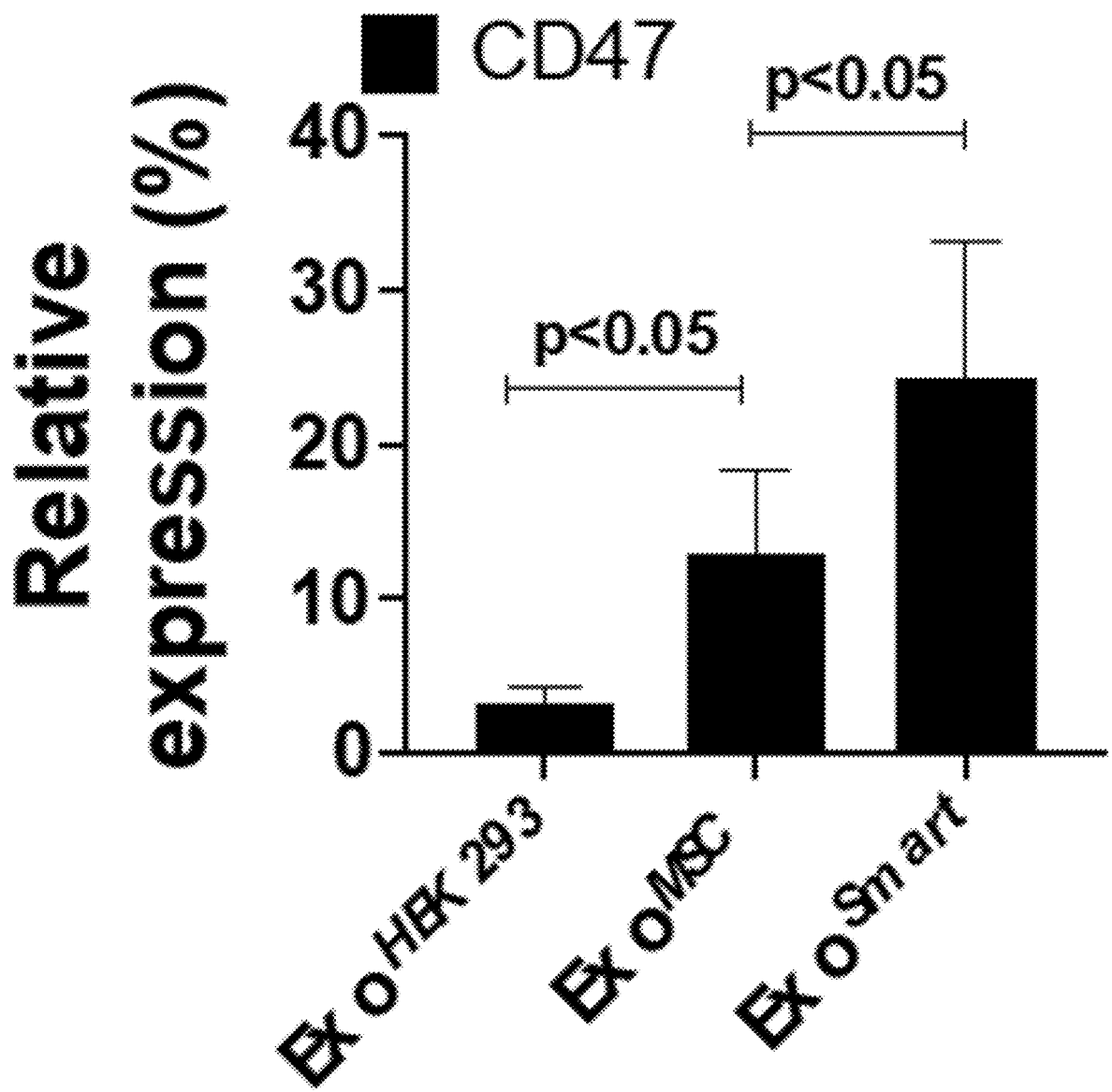

Smart exosomes having a round shape and a size of 100 nm were prepared, as seen in FIG. 10C. The $Exo^{Smart}$ featured exosomal biomarkers as well as HA-RGD and $CD47^{p110-130}$-FLAG expression as determined by western blot. The size of the $Exo^{Smart}$ exosomes was confirmed by conventional transmission electron microscopy (C:TEM). The $Exo^{Smart}$ displaying HA and FLAG peptides were also validated by ELISA (FIG. 10B) and flow cytometry (FIGS. 10D, 10E) assays.

The $Exo^{Smart}$ exosomes were evaluated in mice. The tumors from $Exo^{Smart}$, $Exo^{HA-RGD}$, and $Exo^{HA}$ injected PDCL5/PSC mice were stained with anti-fibronectin, anti-αvβ3, anti-HA, and HE. The $Exo^{Smart}$ exosomes were seen to penetrate the extracellular matrix in the tumor microenvironment and target αvβ3 expressing cells. (FIGS. 1A-11C.) The $Exo^{Smart}$ group showed stronger HA signal than $Exo^{HA-RGD}$ and $Exo^{HA}$. Strong fibronectin-staining was also shown in the $Exo^{Smart}$ group.

A phagocytosis assay was conducted, and showed that phagocytosis in PMA-induced THP-1 cells was significantly inhibited by exosomes displaying $Exo^{Smart}$. (FIGS. 12A-12E.) The expression of $CD9^{CD47p110-130}$ on $Exo^{Smart}$, and CD47 on $Exo^{CD7}$ and $Exo^{MSC}$ was determined by western blot detecting FLAG and CD47.

Figure 13A:
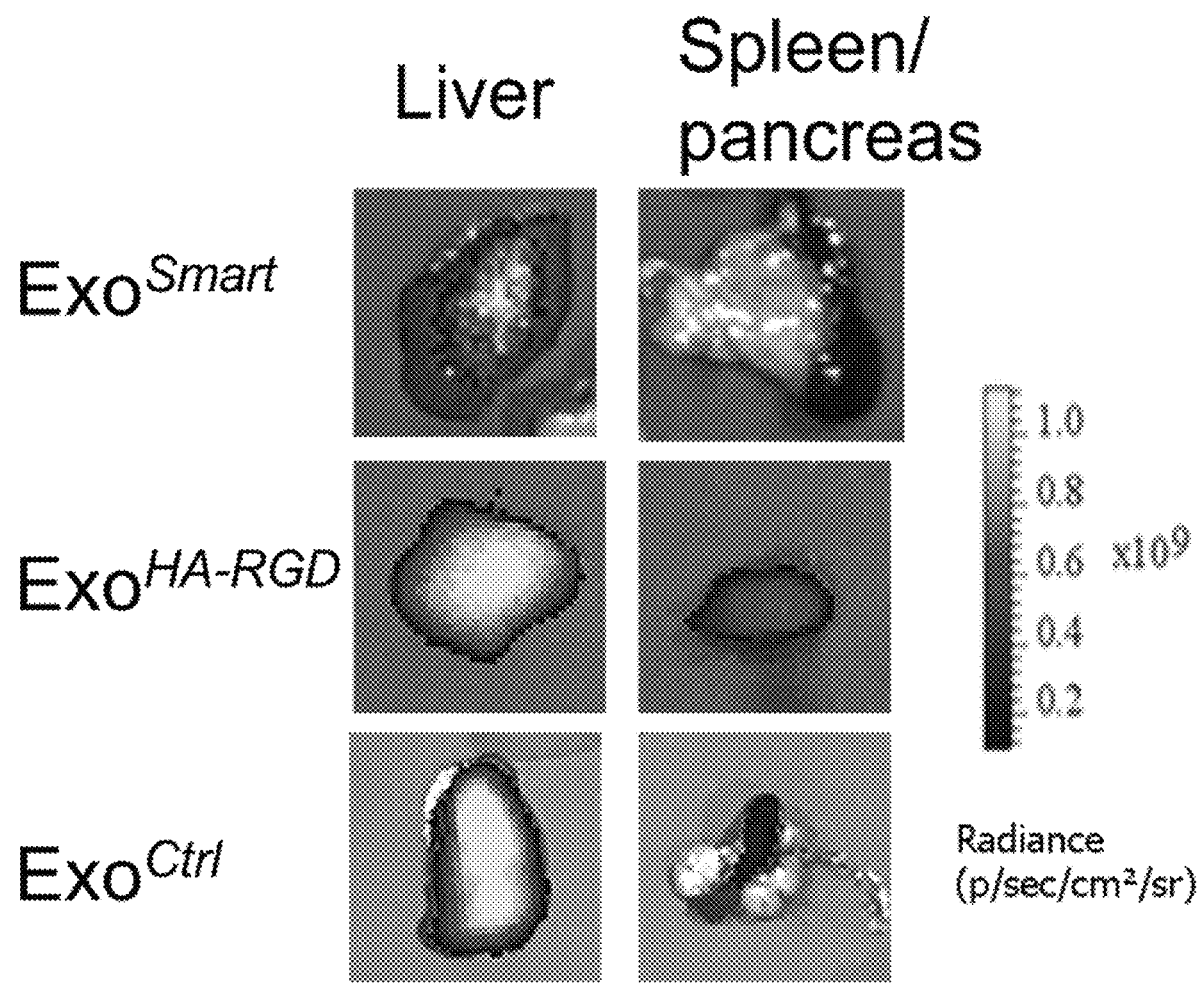
FIGS. 13A-13C: In vivo delivery of DiR-labeled exosomes demonstrates a decreased Exo$^{Smart}$ accumulation in the liver and spleen as compared to that of Exo$^{HA-RGD}$ and Exo$^{Ctrl}$ (FIG. 13A). Quantitative analysis showed significance (FIG. 13B, p<0.05). This was also confirmed by immunofluorescence analysis of tissues from the liver, spleen, and pancreas using anti-HA (red color) (FIG. 13C). Scale bar: 50 μm.
Figure 13B:
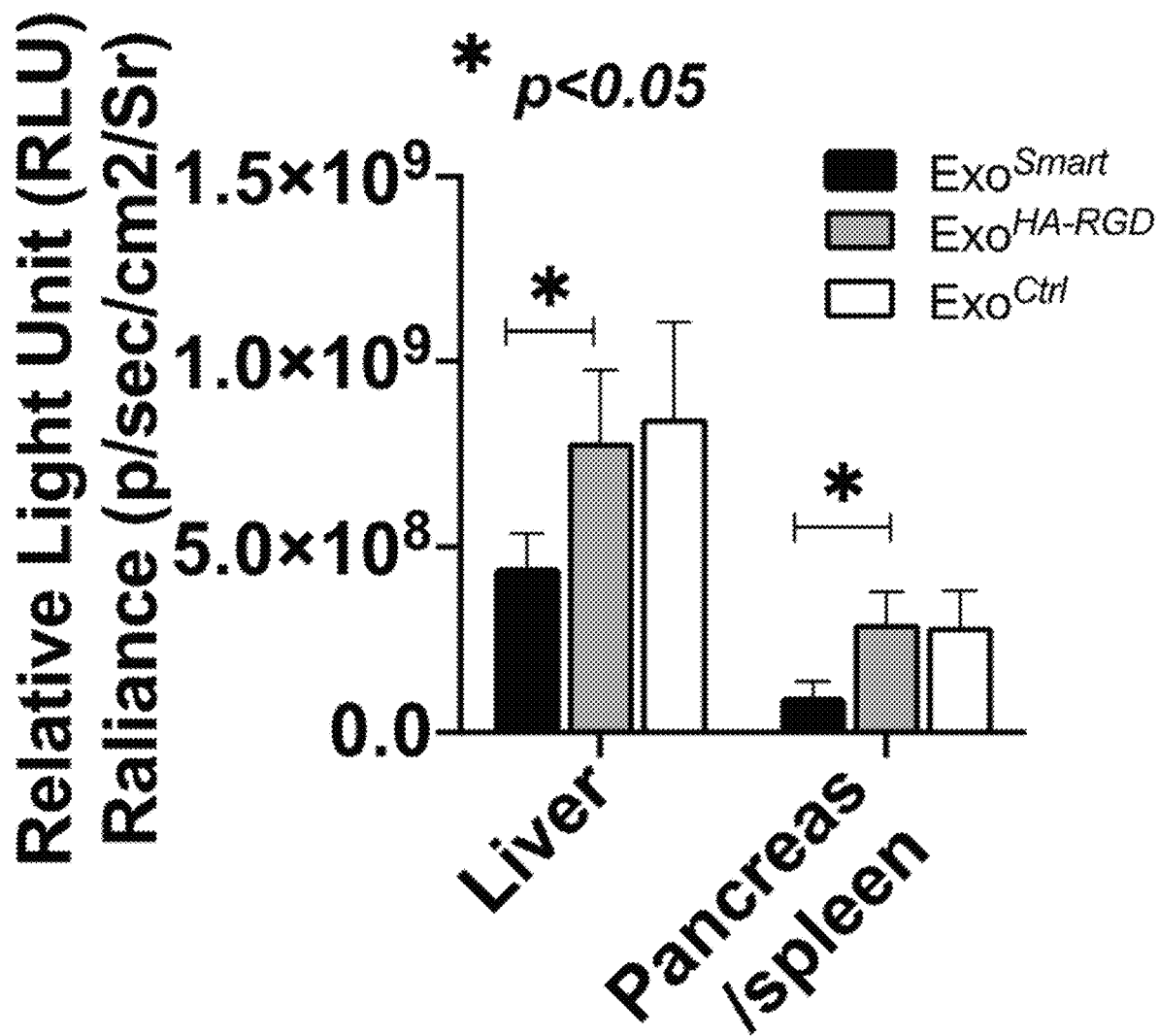
Figure 13C:
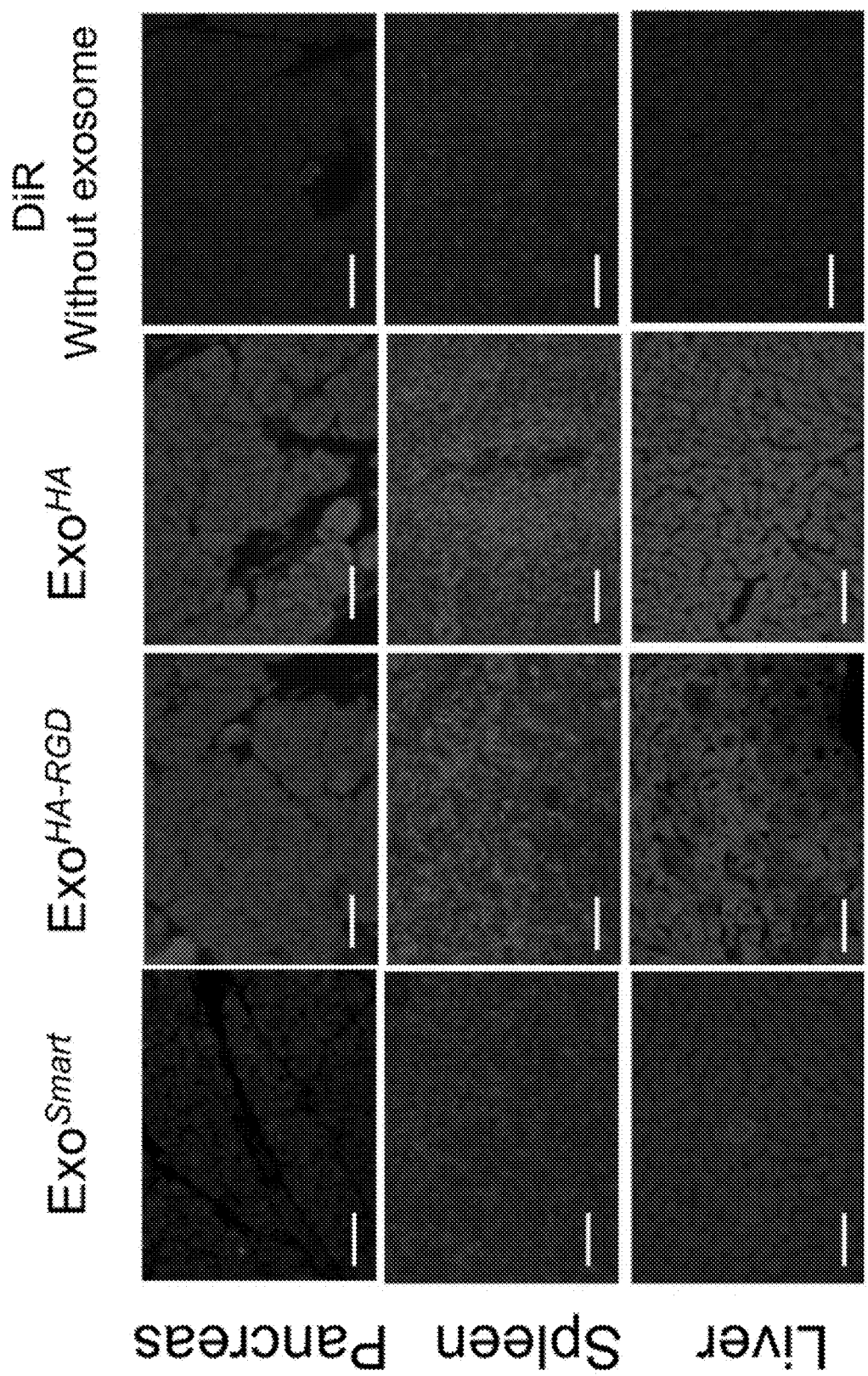

Organ imaging from the mice showed that in vivo delivery of DiR-labeled exosomes demonstrated a decreased $Exo^{Smart}$ accumulation in the liver and spleen as compared to that of $Exo^{HA-RGD}$ and $Exo^{Ctrl}$ (FIGS. 13A-13B). This was also confirmed by immunofluorescence analysis of tissues from the liver, spleen, and pancreas using anti-HA (red color in FIG. 13C).

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

---

What is claimed is:

1. A composition comprising an exosome that expresses a peptide on a surface of the exosome, wherein the peptide is incorporated into a CD9 protein between a E174 residue and a T175 residue of the CD9 protein, and wherein the peptide consists of $CD47^{p110-130}$.

2. A composition comprising an exosome that expresses a peptide on a surface of the exosome, wherein the peptide is incorporated into a CD9 protein between a E174 residue and a T175 residue of the CD9 protein, further comprising a second peptide expressed on the surface of the exosome, wherein the second peptide comprises $CD47^{p110-130}$ and is incorporated into a second CD9 protein at a E174 residue or V178 residue of the second CD9 protein.

3. The composition of claim 2, wherein the second peptide is incorporated into an extracellular loop of the second CD9 protein.

4. The composition of claim 2, wherein the second peptide is incorporated into a variable region of a large extracellular loop of the second CD9 protein.

5. The composition of claim 2, wherein the second peptide is incorporated at the E174 residue of the second CD9 protein.

6. The composition of claim 2, wherein the second peptide is incorporated at the V178 residue of the CD9 protein.

7. The composition of claim 2, wherein the first peptide comprises (Currently Amended) RGD.

8. A method of delivering a drug to pancreatic cancer cells, the method comprising:
    loading the exosome of the composition of claim 7 with a drug to obtain a drug-loaded exosome; and
    administering the drug-loaded exosome to a subject having pancreatic cancer to deliver the drug to pancreatic cancer cells while avoiding clearance by macrophages.

9. The method of claim 8, wherein the drug comprises a small molecule, a protein, a peptide, a mRNA, a miRNA, a RNAi, an oligonucleotide, or a combination thereof.

10. The method of claim 8, wherein the drug is a chemotherapeutic agent.

11. The method of claim 8, wherein the drug comprises paclitaxel, 5-fluorouracil, abraxane, afinitor, erlotinib hydrochloride, everolimus, gemcitabine hydrochloride, oxaliplatin, capecitabine, cisplatin, irinotecan, colinic acid, folfox, folfirinox, nab-paclitaxel with gemcitabine, metformin, digoxin, simvastatin, or a combination thereof.

12. The composition of claim 2, wherein:
the first peptide comprises RGD; and
the exosome further comprises a chemotherapeutic agent encapsulated therein.

13. The composition of claim 2, wherein:
the first peptide comprises RGD; and
the exosome further comprises paclitaxel encapsulated therein.

14. A method for making exosomes that display a peptide, the method comprising:
modifying a first CD9 protein between a E174 residue and a T175 residue of the first CD9 protein with a first peptide to form a first modified CD9 protein;
transfecting HEK 293 cells with a vector expressing the first modified CD9 protein;
harvesting exosomes from a cell culture medium of the transfected HEK 293 cells; and
purifying the harvested exosomes to obtain exosomes displaying the first peptide;
wherein the method further comprises modifying a second CD9 protein at a E174 residue or V178 residue of the second CD9 protein with a second peptide comprising $CD47^{p110-130}$ to form a second modified CD9 protein, and the step of transfecting the HEK 293 cells with a vector expressing the second modified CD9 protein, wherein the obtained exosomes express the second peptide.

* * * * *

UNITED STATES PATENT AND TRADEMARK OFFICE
CERTIFICATE OF CORRECTION

PATENT NO. : 12,090,213 B2
APPLICATION NO. : 18/550503
DATED : September 17, 2024
INVENTOR(S) : Shi-He Liu and Francis Charles Brunicardi It is certified that error appears in the above-identified patent and that said Letters Patent is hereby corrected as shown below:

In the Claims

Please correct Column 18, Claim 7, Lines 59, and 60 from:
"The composition of claim 2, wherein the first peptide comprises (Currently Amended) RGD."
To:
--The composition of claim 2, wherein the first peptide comprises RGD.--

Signed and Sealed this
Twenty-sixth Day of November, 2024

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Asp Cys Arg Gly Asp Cys Phe Cys
1               5

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asn Tyr Thr Cys Glu Val Thr Glu Leu Thr Arg Glu Gly Glu Thr
1               5                   10                  15

Ile Ile Glu Leu Lys
            20

<210> SEQ ID NO 3
<211> LENGTH: 54
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tacccatacg atgttccaga ttacgcttgc gattgccgtg gcgattgctt ttgc          54

<210> SEQ ID NO 4
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaaactaca cttgtgaagt aacagaatta accagagaag gtgaaacgat catcgagcta   60
aaagattaca aggatgacga cgataag                                       87

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Tyr Asp Val Pro Asp Tyr Ala Cys Asp Cys Arg Gly Asp Cys
1               5                   10                  15

Phe Cys

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asn Tyr Thr Cys Glu Val Thr Glu Leu Thr Arg Glu Gly Glu Thr
1               5                   10                  15

Ile Ile Glu Leu Lys Asp Tyr Lys Asp Asp Asp Lys
                20                  25
```